United States Patent
Fritzsch et al.

(10) Patent No.: US 11,911,416 B2
(45) Date of Patent: Feb. 27, 2024

(54) COMPOSITIONS AND METHODS TO RESTORE HEARING LOSS AND BALANCE THROUGH EMBRYONIC EAR TRANSPLANT

(71) Applicant: University of Iowa Research Foundation, Iowa City, IA (US)

(72) Inventors: Bernd Fritzsch, Iowa City, IA (US); Karen Elliott Thompson, Cedar Rapids, IA (US); Marlan Hansen, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 897 days.

(21) Appl. No.: 16/529,186

(22) Filed: Aug. 1, 2019

(65) Prior Publication Data
US 2020/0061120 A1    Feb. 27, 2020

Related U.S. Application Data

(60) Provisional application No. 62/713,250, filed on Aug. 1, 2018.

(51) Int. Cl.
| | |
|---|---|
| *A61K 35/12* | (2015.01) |
| *A61K 35/36* | (2015.01) |
| *C12N 5/073* | (2010.01) |
| *A61N 1/05* | (2006.01) |

(52) U.S. Cl.
CPC .............. *A61K 35/36* (2013.01); *A61K 35/12* (2013.01); *A61N 1/0541* (2013.01); *C12N 5/0603* (2013.01)

(58) Field of Classification Search
None
See application file for complete search history.

(56) References Cited

U.S. PATENT DOCUMENTS

| | | | |
|---|---|---|---|
| 9,572,815 | B2 | 2/2017 | Zuo et al. |
| 9,896,658 | B2 | 2/2018 | Edge |
| 2017/0029511 | A1 | 2/2017 | Saragovi et al. |
| 2017/0029822 | A1 | 2/2017 | Saragovi et al. |
| 2017/0042842 | A1 | 2/2017 | Edge et al. |
| 2017/0095481 | A1 | 4/2017 | Edge et al. |
| 2017/0314027 | A1 | 11/2017 | Edge et al. |
| 2017/0327557 | A1 | 11/2017 | Chen |
| 2018/0087026 | A1 | 3/2018 | Rivolta et al. |

OTHER PUBLICATIONS

Kobashigawa, J., Ann Thorac Surg. Mar. 2022;113(3):711 (Year: 2022).*
DMEM Thermo Fischer Scientific downloaded from https://www.thermofisher.com/us/en/home/life-science/cell-culture/mammalian-cell-culture/cell-culture-media/dmem.html on Dec. 19, 2022 (Year: 2022).*
Kojima et al., Acta Otolaryngol Suppl. Mar. 2004;(551):53-55 (Year: 2004).*
Ahmed, Hena , et al., "Emerging Gene Therapies for Genetic Hearing Loss", Journal of the Association for Research In Otolaryngology vol. 18, Aug. 16, 2017, 649-670.
Balkany, Thomas J, et al., "The Ear Book: A Complete Guide to Ear Disorders and Health", 2017 https://books.google.com/books?hl=en&lr=&id=OCfJDgAAQBAJ&oi=fnd&pg=PP1&dq=Congenital+hearing+loss,+congenital+balance+loss,+ear+transplantation,+hearing+restoration,+vestibular+restoration&ots=su2XTuUin3&sig=souSW1JXqamsq6smJbLqHhKipjl#v=onepage&q&f=false,.
Eggermont, Jos J, "Hearing Loss Causes, Prevention, and Treatment" Feb. 22, 2017, 1-426 https://books.google.com/books?d=fJExDQAAQBAJ&newbks=1&newbks_redir=0&lpg=PP1&pg=PP1#v=onepage&q&f=false.
Elghouche, Alhasan N., et al., "Chapter 4: Inner Ear Organoids: Recapitulating Inner Ear Development in 3D Culture", Organ Regeneration Based on Developmental Biology, Springer Nature Singapore Pte Ltd., Mar. 31, 2017, 57-72.
Elliott, Karen L., et al., "Ear transplantations reveal conservation of inner ear afferent pathfinding cues", Scientific Reports vol. 8(13819), Sep. 14, 2018, 1-12.
Gordy, Clayton , et al., "Caudal Transplantation of Ears Provides Insights into Inner Ear Afferent Pathfinding Properties", Developmental Neurobiology, Jul. 3, 2018, 1-17.
Hussain, Basharat , et al., "Hearing Impairments, presbycusis and the possible therapeutic interventions", Biomedical Research & Therapy, vol. 4(4), Apr. 20, 2017, 1228-1245.
Meas, Steven J, et al., "Reprogramming Glia Into Neurons in the Peripheral Auditory System as a Solution for Sensorineural Hearing Loss: Lessons From The Central Nervous System", Frontiers in Molecular Neuroscience vol. 11(77), Mar. 14, 2018, 1-12.
Mittal, Rahul , et al., "Recent Advancements in the Regeneration of Auditory Hair Cells and Hearing Restoration", Frontiers in Molecular Neuroscience vol. 10, Jul. 31, 2017, 1-16.
Munnamalai, Vidhya , et al., "Building the human inner ear in an organoid", Nature Biotechnology vol. 35, Jun. 7, 2017, 518-520.

\* cited by examiner

*Primary Examiner* — Daniel C Gamett
(74) *Attorney, Agent, or Firm* — DENTONS DAVIS BROWN PC; Matthew Coryell

(57) ABSTRACT

Described herein is a method for treating or restoring loss of hearing and balance in a subject in need thereof. In certain aspects, the disclosed method is comprised of transplanting a humanized otocyst to a target delivery site in the subject. According to certain aspects, the otocyst is obtained from a humanized non-human mammal embryo. In certain exemplary aspects, the non-human mammal is a pig. In certain embodiments, prior to transplantation, the otocyst is cultured in a species-specific tissue culture buffer.

14 Claims, 12 Drawing Sheets

COMPOSITIONS AND METHODS TO RESTORE HEARING LOSS AND BALANCE THROUGH EMBRYONIC EAR TRANSPLANT

CROSS-REFERENCE TO RELATED APPLICATION(S)

This application claims priority from U.S. Provisional Application Ser. No. 62/713,250, filed Aug. 1, 2018, and entitled "COMPOSITIONS AND METHODS TO RESTORE HEARING LOSS AND BALANCE THROUGH EMBRYONIC EAR TRANSPLANT," which is hereby incorporated herein by reference in its entirety.

BACKGROUND

The disclosure relates to compositions and methods for the restoration of hearing loss. Hearing loss is predicted to reach almost 1 billion people worldwide by 2050 (WHO). Outside of cochlear implants, attempts at restoring hearing after sensorineural hearing loss have been unsuccessful. Accordingly, there is a need in the art for improved modes of treatment for the restoration of hearing loss.

BRIEF SUMMARY

Described herein is a method for treating or restoring loss of hearing and balance in a subject in need thereof. The disclosed method is comprised of transplanting a humanized otocyst to a target delivery site in the subject. According to certain aspects, the otocyst is obtained from a humanized non-human mammal embryo. In certain exemplary aspects, the non-human mammal is a pig. In certain embodiments, prior to transplantation, the otocyst is cultured in a species-specific tissue culture buffer.

According to certain aspects, the delivery site is the vestibule of the inner ear of the subject. In certain exemplary aspects of these embodiments, the method further comprises removing of the stapes footplate of the subject prior to the transplantation of the otocyst.

According to certain further aspects, the delivery site is the internal auditory canal of the subject.

According to still further aspects, the delivery site is the cerebellopontine angle adjacent to axons of cranial nerve VIII.

According to yet further embodiments, the delivery site is proximate to the jugular foramen. In exemplary aspects of these embodiments, the delivery site adjacent to the rootlets of cranial nerves IX and X. In still further aspects of these embodiments, the method further comprises exposing the delivery site by performing a retrosigmoid or infratemporal fossa craniotomy.

In certain exemplary embodiments, the dorsoventral, mediolateral, and anteroposterior orientation of the otocyst is maintained relative to the target delivery site of the subject.

In further aspects, the method further comprises implanting a cochlear implant electrode to activate the inner ear of the subject. In certain exemplary aspects of these embodiments, the method further comprises implanting a osseointegrated bone conduction hearing aid in the subject to augment inner ear activation.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

Figure 1:
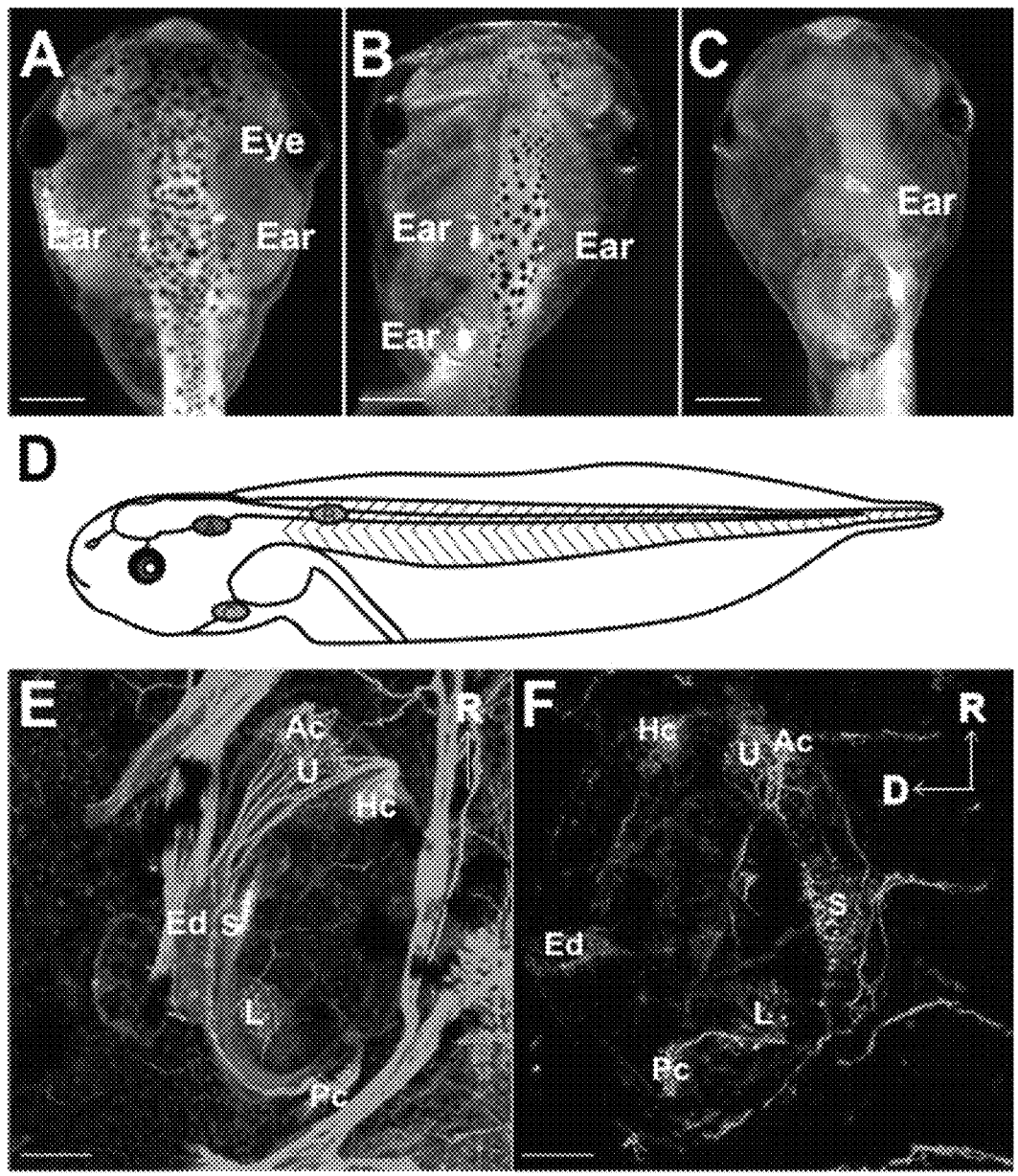
FIG. 1. Evaluation of ear transplantations (A-D) Stage 46 *X. laevis* embryos showing positions of native ears and transplanted ears (circled). (A) Control animal. (B) Embryo with a third ear transplanted adjacent to the spinal cord. (C) Ventral view of embryo with a third ear transplanted next to the heart. (D) Schematic diagram representing a lateral view of stage 46 *X. laevis* demonstrating the positions of the native ear (red, A) and the two different transplantations (green, B,C). (E) Control ear and (F) a transplanted ear labeled with antibodies against MyoVI (red) and tubulin (green) demonstrating the presence of hair cells in six distinct epithelia along with Hoechst nuclei counterstain (blue) (Utricle, U; Saccule, S; Lagena, L; Anterior canal, Ac; Horizontal canal, Hc; Posterior canal, Pc) and neurons, respectively. Endolymphatic duct is labeled Ed. Scale bars in A-C are 0.5 mm and 100 µm in E-F.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used herein, the term "subject" used throughout the specification to describe an animal, human or non-human, to whom treatment according to the methods of the present invention is provided. Veterinary and non-veterinary applications are contemplated. The term includes, but is not limited to, birds and mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs. Thus, adult and newborn subjects, whether male or female, are intended to be covered. In one aspect, the subject is a mammal. A patient refers to a subject afflicted with a disease or disorder (e.g. deafness or hearing loss). The term "patient" includes human and veterinary subjects. In some aspects of the disclosed methods, the subject has been diagnosed with a need for treatment for hearing loss in one or both ears.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human.

As used herein, "humanized" refers to an organ or tissue harvested from a non-human animal whose protein sequences and genetic complement are more similar to those of humans than the non-human host.

As used herein, the term "targeted delivery site," or "delivery site," refers to a location in the body (i.e. body space) where a otocyst transplant or other therapeutic composition is administered in a manner and amount intended to produce a desired therapeutic effect. One skilled in the art will appreciate that suitable delivery sites for otocyst transplant will depend on the condition, disorder or injury that is being treated.

The anatomy of the ear is well known to those of ordinary skill in the art (see, e.g., Gray's Anatomy, Revised American Edition (1977), pages 859-867, incorporated herein by reference). The ear is generally divided into three portions: the outer ear, middle ear, and inner ear. The outer ear is composed of the pinna, the auditory canal, and the outward facing portion of the tympanic membrane (ear drum). The function of the outer ear, in part, is to collect and direct sound waves through the auditory canal towards the tympanic membrane and the middle ear.

The middle ear is an air-filled cavity that includes the tympanic cavity, three ear bones (auditory ossicles): the malleus, the incus and the stapes, and oval window, which connects the middle ear with the inner ear. The auditory ossicles are arranged to provide a mechanical linkage between the tympanic membrane and the oval window to the fluid-filled inner ear, where sound is transformed and transduced to the inner ear for further processing.

The inner ear includes three sensory portions: the cochlea, which senses sound; the semicircular canals, which sense angular acceleration; and the otolithic organs (utricle and saccule), which sense linear acceleration; and the round window that connects the cochlea to the middle ear. In each of these sensory portions, specialized sensory hair cells are arrayed upon one or more layers of inner ear supporting cells. Supporting cells underlie, at least partially surround, and physically support sensory hair cells within the inner ear. In operation, the sensory hair cells are physically deflected in response to sound or motion, and their deflection is transmitted to nerves which send nerve impulses to the brain for processing and interpretation.

In particular, the cochlea includes the Organ of Corti which is primarily responsible for sensing sound. The Organ of Corti includes a basilar membrane upon which are located a variety of supporting cells, including border cells, inner pillar cells, outer pillar cells, inner phalangeal cells, Deiters' cells and Hensen's cells. Supporting cells support inner hair cells and outer hair cells. The tectorial membrane is disposed above inner hair cells and outer hair cells.

Harvesting of Otocysts

According to certain embodiments, Otocysts are obtained from humanized pigs, or other vertebrate that hears at a similar frequency range as humans, at a stage equivalent to the developing mouse ear between embryonic day 9.5-10.5 of development. To obtain embryos, timed pregnant pigs (or other mammal) are sacrificed and the embryos will be removed. In exemplary aspects, otocysts will be dissected out according to methods known in the art. Otocysts are then transferred and maintained in a species-specific tissue culture buffer on ice in sterile conditions until transplant.

Target Delivery Sites

According to certain embodiments, the disclosed method transplant the otocyst into the vestibule of the inner ear. In certain aspects of this embodiment, removal of the stapes footplate is performed to facilitate access of the target delivery site. While providing a more restricted space for implantation than other embodiments, this would allow the closest approximation for inner ear nerve fibers to grow along any remaining VIIIth nerve axons as the otocyst will completely replace part of the existing non-functioning ear.

In a second exemplary embodiment, the otocyst is transplanted in the internal auditory canal or cerebellopontine angle (CPA) adjacent to the existing VIIIth nerve axons. This provides access to these nerve fibers and has more space for the developing inner ear than that provided by transplantation into the otic capsule. As will be appreciated to those skilled in the art, several surgical approaches to the internal auditory canal/CPA exist including middle fossa, translabyrinthine, and retrosigmoid approaches.

In a third exemplary embodiment, the otocyst is transplanted to a target deliver site adjacent to the rootlets for lower cranial nerves (glossopharyngeal, CNIX and vagus, CNX) near the jugular foramen. In Exemplary embodiments, exposure is accomplished through a retrosigmoid or infratemporal fossa craniotomy. This approach also provides ample room for a developing otocyst and access to the hindbrain via existing cranial nerves. Without wishing to bound to any particular theory, the rationale for using this site is that inner ear nerve fibers could grow along existing cranial nerves to reach the hindbrain. As disclosed herein, the inner ear afferents reroute to the vestibular and cochlear nuclei if they reach the hindbrain in close proximity to these nuclei. Furthermore, this site is ideal should any remaining VIIIth nerve fibers or myelin scaffolding be absent.

In any of the foregoing exemplary embodiments, the otocyst is preferably transplanted to maintain dorsoventral, mediolateral, and anteroposterior orientations for proper function of the vestibular system.

The disclosed transplanted otocysts have a self-contained developmental system with all the necessary information to develop into a fully functional inner ear that also can recruit surrounding mesenchyme to form an otic capsule. According to further embodiments, the transplanted otocyst is supplemented through the use of human stem cells derived embryoids known to form hair cells in tissue culture. Combining this approach with an otocyst imposes the necessary organizational information to these organoids to become fully incorporated in the otocyst.

The transplanted and normally oriented ear will provide vestibular information to help maintain balance. According to certain embodiments, in order supply auditory information, a bone conduction hearing aid (osseointegrated or head band) is employed to directly activate the inner ear. According to certain alternative embodiments, a cochlear implant electrode and system to provide sound related information to the transplanted ear.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

Animals

Xenopus laevis embryos of either sex were obtained through induced ovulation by injection of human chorionic gonadotropin, followed with fertilization by sperm suspension in 0.3× Marc's Modified Ringer's Solution (MMR, diluted from 10× stock; 1M NaCl, 18 mM KCl, 20 mM CaCl2, 10 mM MgCl2, 150 mM HEPES, pH 7.6-7.8). The jelly coat was removed with 2% cysteine in 0.1×MMR. Embryos were incubated in 0.1×MMR until having reached the desired stage for manipulation (see below), and until desired stages for tracing, behavior and physiological experiments (described below) as described by Nieuwkoop and Faber (1994).

Ear Transplantations

All surgical manipulations were performed in 1.0×MMR at room temperature. Animals were anesthetized with 0.02% Benzocaine (Crook and Whiteman, 2006) prior to and during all manipulations. Otic placodes and otic vesicles from donor embryos were removed and transplanted to recipient hosts at stage 25-27 and 28-36, respectively. Removed placodes or vesicles were grafted adjacent to the spinal cord in place of a removed somite on one side of the embryo. Additionally, otic vesicles from stage 32-36 donor embryos were transplanted to the ventral heart region, in the vicinity of the vagus nerve trajectory. Embryos were kept in 1.0×MMR after surgery for 15-30 minutes to allow healing. Animals were then transferred into 0.1×MMR. Animals to be used for behavioral and physiological assays were processed as below. Animals used only for immunohistochemistry and dye labeling were allowed to grow until stage 46, and subsequently anesthetized in 0.02% Benzocaine and fixed by immersion in either 4% paraformaldehyde (PFA), when used for immunohistochemistry or dextran tracing, or in 10% PFA when used for lipophilic dye tracing (see below). Successful development of the ear was confirmed at stage 46 based on the presence or absence of an ear in the region of transplantation and by the presence of otoconia. Ear development was further assessed using anti-Myo6 antibody to label hair cells and anti-tubulin antibody to label nerve fibers (see immunochemical analysis below). Only animals with fully formed transplanted ears, as indicated by otoconia in position above sensory epithelia, were used for further analysis.

C-Start Startle Assay and Analysis

For startle response testing, donor ears were transplanted to the trunk at stage 25-27 as described above, but at a slightly more rostral position along the spinal cord. At stage 40-42, the native two ears were removed. For controls, both native ears were removed at stage 40 from animals that did not have an ear transplanted to the trunk. This time point of stage 40-42 was selected since nearly all Mauthner cells, the cells in the hindbrain that drive the c-start startle response from inner ear stimulation survive with ear removal at stage 40 (Elliott et al., 2015a). Animals were allowed to grow until stage 46. Tadpoles were placed individually in a 50 mm diameter Petri dish containing 0.1×MMR for the startle assay. Startle responses were elicited from dropping a 3.5 kg standardized object from a 12 cm height onto a sturdy lab bench, adjacent to the Petri dish containing the tadpole. Subsequent C-start startle response behavior was video recorded in slow-motion from a fixed distance directly above the Petri dish. Each of 13 control animals and 15 animals with transplanted ears were subjected to four trials and the presence or absence of a response, as well as the initial direction of the response, if present, was documented. Significance of direction of turn was calculated using a Chi-Square analysis with Microsoft Excel. Following behavioral analysis, animals were anesthetized in 0.02% Benzocaine and fixed by immersion 10% PFA as described above and were then processed for lipophilic dye labeling.

Electrophysiology

Following ear transplantations at stage 28-29 (see above), *Xenopus laevis* tadpoles of either sex were obtained from the in-house animal breeding facility at the Biocenter-Martinsried at the Biomedical Center of the Ludwig-Maximilians-University Munich. Tadpoles were kept in tanks filled with 17-18° C. non-chlorinated water at a 12/12 light/dark cycle. A total of 5 animals at developmental stages 54-57 were used for recordings of neuronal activity. Experiments were performed in vitro on isolated, semi-intact preparations and comply with the National Institute of Health publication entitled "Principles of animal care", No. 86-23, revised 1985. Permission for these experiments was granted by the governmental institution at the Regierung von Oberbayern/Government of Upper Bavaria (55.2-1-54-2532-14-2016; 55.2-1-54-2532.0-24-2017).

For all experiments, tadpoles were anesthetized in 0.05% 3-aminobenzoic acid ethyl ester (MS-222; Pharmaq Ltd., United Kingdom) in frog Ringer (75 mM NaCl, 25 mM $NaHCO_3$, 2 mM CaCl2, 2 mM KCl, 0.5 mM MgCl2, and 11 mM glucose, pH 7.4) and decapitated ~10 segments below the transplanted ear. The skin above the head was removed, the skull and rostral vertebrae opened, and the forebrain disconnected. This surgical procedure preserved all inner ear organs, the central nervous system and the extraocular motor innervation and allowed natural and galvanic stimulation of vestibular endorgans and recording of extraocular motor responses.

Extracellular multi-unit spike discharge from severed extraocular motor nerves was recorded with glass suction electrodes from the cut end of the extraocular motor nerves. Glass microelectrodes were made with a horizontal puller (P-87, Sutter Instruments Co., USA) and were individually adjusted at the tip to fit the diameter of the respective target nerves. Extraocular motor nerve activity was recorded (EXT 10-2F; npi electronic GmbH, Germany), digitized at 10-20 kHz (CED 1401, Cambridge Electronic Design Ltd., United Kingdom) and stored on a computer for offline analysis. For the analysis, responses obtained during 20-120 repetitions of sinusoidal turntable oscillations or sinusoidally modulated current stimuli (see below) were averaged to obtain the mean response±standard error of the mean (SEM) over a single cycle.

Motion and Galvanic Vestibular Stimulation (GVS)

The recording chamber with the semi-intact *Xenopus* preparations was mounted on a computer-controlled, motorized two-axis turntable (ACT-1002, Acutronic USA Inc., Switzerland) with the preparation centered in the horizontal and vertical rotation axes to provide optimal activation of semicircular canal organs. Motion stimuli consisted of sinusoidal rotations across frequencies that ranged from 0.2 to 1 Hz (peak velocities: ±12-60°/s). Sinusoidally modulated galvanic currents were applied by stimulus electrodes that consisted of two Teflon-coated silver wires (diameter: 0.76 mm; AG 25-T, Science Products GmbH, Germany), placed on the outer surface of the native otic capsules or the transplanted third ear. The two stimulus electrodes were cut at the tip, chlorinated to minimize polarization, and separately attached to a micromanipulator, to enable precise positioning under visual guidance. For most experiments, electrodes were placed bilaterally in close proximity of the visible cupulae of a specific bilateral coplanar semicircular canal pair (e.g. left posterior and right anterior semicircular canal). To stimulate the third ear, one electrode was placed on the outer surface of the visible otic capsule and the second electrode at a distance of ~10 mm from the first in the Ringer solution of the recording chamber. Sine waves for the GVS were produced with a linear stimulus isolator (WPI A395, World Precision Instruments Inc., USA), triggered by the analog output from an analog/digital converter (CED 1401). The galvanic currents were applied to the two electrodes in phase-opposition (Gensberger et al., 2016) and consisted of sinusoidally modulated currents at frequencies of 0.2-1 Hz and magnitudes of ±50-200 µA for GVS of the native semicircular canals and of ±200-500 µA for GVS of the third ear.

Lipophilic Dye Labeling

Axonal projections from transplanted ears were labeled using NeuroVue lipophilic dyes. NeuroVue™ Maroon, NeuroVue™ Red, and NeuroVue™ Jade (Polysciences, Inc.) dye-soaked filter paper pieces were cut to fit and were placed inside transplanted ears. Care was taken to place the dye on regions of sensory epithelia as determined by location of otoconia. Dye placed in transplanted ears labels inner ear afferent axons through backfilling of dendritic processes, terminating on hair hells, into ganglion cell bodies. Dye was also placed into the spinal cord following transection, either rostral or caudal, to the adjacently transplanted ear to fill inner ear afferent axonal processes within the spinal cord as they project within it and into the hindbrain. To determine lateral line innervation of an ear transplanted adjacent to the spinal cord, dye was placed into the posterior lateral line ganglia caudal and adjacent to the native ear, filling lateral line afferents to neuromast (lateral line) organs along the trunk of the animal. In the same animals, dye was placed into the spinal cord to label afferents entering the CNS. Native ear afferent projections into the hindbrain were labeled with dye inserted into each native ear. Following dye insertions, animals were kept in 0.4% paraformaldehyde and incubated at 60° C. or 36° C. to permit diffusion. Dye placed in the spinal cord or posterior lateral line ganglia were incubated at 60° C. for 60 hours. Dye placed into transplanted ears near the spinal cord were incubated for 18 hours at 36° to determine the spinal cord entry point or for 60 hours at 60° to assess hindbrain innervation. Ears transplanted to the heart region were labeled with dye insertions either into the transplanted ear or into the vagus nerve directly and were incubated for 3 days at 60°. Native ear dye placements were incubated for 18 hours at 36°. Following diffusion, the brain and spinal cord was dissected out and the specimens were mounted in glycerol for imaging on a TCS SP5 Multi-photon confocal microscope using excitation emission settings specific for the different lipophilic dyes used.

Dextran Amine Labeling

Dextran amine dye injections into ears transplanted adjacent to the spinal cord were used to evaluate inner ear afferent projection in the CNS. Entry points of inner ear afferents into the spinal cord as well as their projections into the hindbrain were evaluated using Texas red, tetramethylrhodamine, Alexa Fluor 647, and Alexa Fluor 488 dye (Molecular Probes). A small incision was made into the transplanted ear of anesthetized animals (0.02% Benzocaine) and a recrystallized drop of the labeling dye on a tungsten needle was inserted. Care was taken to fill the ear entirely with the dye. Animals were washed in 0.1×MMR three times in succession and kept in a dish containing 0.1×MMR for 2-3 hours. Afterwards, the embryos were reanesthetized in 0.02% Benzocaine and fixed in 4.0% PFA. After fixation, the brain and spinal cord was dissected out and the specimens were mounted in glycerol for imaging on a TCS SP5 Multi-photon confocal microscope using appropriate excitation/emission filter settings. Dextran amine tracing served to verify lipophilic dye tracing as it is not known to diffuse transcellularly.

Immunohistochemistry

To determine presence of sensory epithelia in transplanted ears, as well as local innervation of the ear and its surroundings, PFA fixed stage 46 animals were dissected to remove the lower jaw and skin and were dehydrated in 70% ethanol overnight. Animals were washed in 1×PBS three times for 10 minutes each before being blocked in 5.0% normal goat serum (NGS) with 0.1% Triton-X 100 for 1 hour. Following a brief wash in 1×PBS, primary antibodies against neuronal marker acetylated tubulin (1:800, Cell Signaling Technology) and against hair cell marker Myosin VI (1:400, Proteus Biosciences) were incubated with the embryos overnight at 36° C. Animals were washed three times for 10 minutes and blocked in 5.0% NGS+0.1% Triton X 100 for 1 hour prior to incubation with species-specific secondary antibodies (1:500, Alexa) along with nuclei marker Hoechst 33342 (Invitrogen) overnight. Animals were washed in 1×PBS six times for 15 minutes each and mounted in glycerol for imaging on a TCS SP5 Multi-photon confocal microscope. In animals where neuromast organs and lateral line afferents were of interest, the skin was kept on during the procedures listed above.

Three-Dimensional Reconstructions

Three-dimensional reconstructions were made from confocal images. Briefly, ears transplanted to the trunk that were immunostained for tubulin and MyoVI as described above were mounted with the trunk lateral side up on a microscope slide in glycerol. In addition, brains from animals in which the transplanted and native ears or the spinal cord and native ears were labeled with lipophilic dye as described above were removed, hemisected along the midline and mounted lateral side up on a slide in glycerol. Confocal z-series images were taken using a Leica TCS SP5 confocal microscope. Z-series stacks were loaded into Amira software (Version 5.4) for manual segmentation. Fibers were individually traced and reconstructed.

Results

Success and Development of Transplantations

Success of transplantations was assessed based on the presence and degree of development of an ear with otoconia at the place of transplantation (FIG. 1). While most transplants were successful in that they developed ears with otoconia, in some instances ears developed without otoconia or formed otoconia-free vesicles, consistent with data from similar placements adjacent to the spinal cord to assess the ability of spinal motor neurons to become efferents to inner ear hair cells. Similar rates of success were found for ears transplanted adjacent to the spinal cord and ventrally near the heart; 83 and 84 percent of animals had transplanted ears with otoconia, respectively (FIG. 1). Only ears that contained otoconia were used for further analysis as presence of otoconia always coincides with hair cell formation. Transplanted ears containing otoconia were examined for degree of development, by immunostaining with antibodies against MyoVI and acetylated tubulin, markers for hair cells and neurons, respectively. Positive MyoVI staining revealed the presence of hair cells in transplanted ears (FIG. 1). Hair cells were found to be in discrete clusters within the ear, indicating distinct vestibular end-organ sensory epithelia formation consistent with near normal ear development. Additionally, tubulin identified neurons and their processes associating with sensory epithelia in the transplanted ears (FIG. 1). These results indicate that ears transplanted in this study are capable of developing hair cells and neurons, similar to those present in native ears and consistent with past work.

Entry and Projection of Afferents in Ears Transplanted to the Spinal Cord

Figure 2:
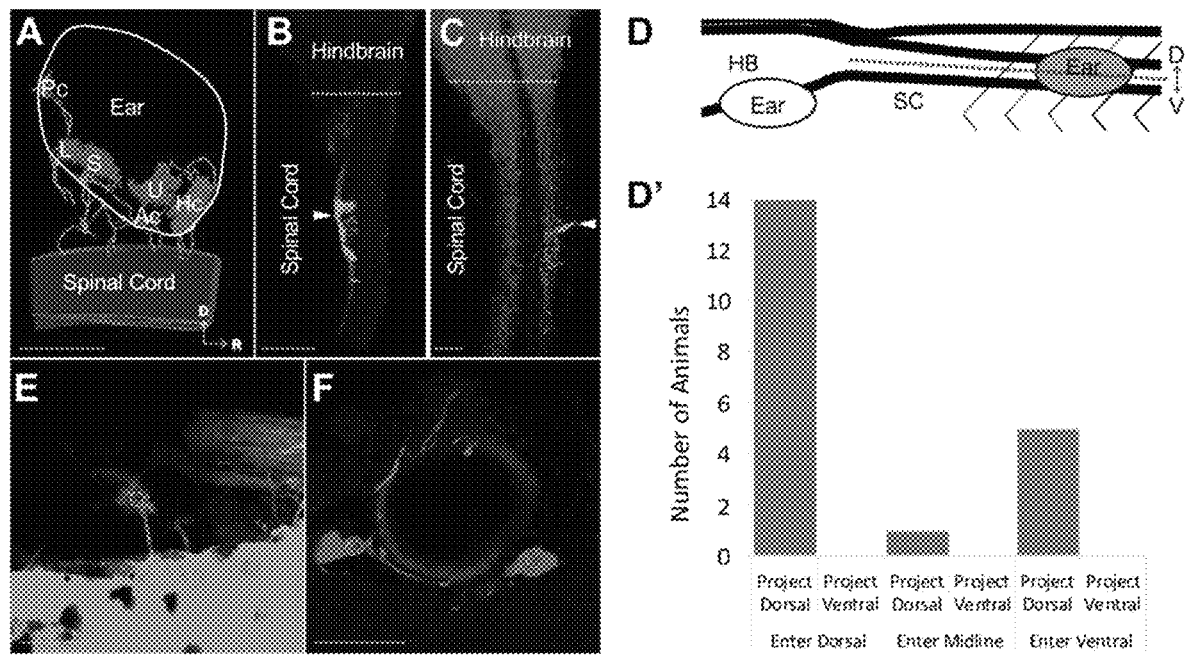
FIG. 2. Ear afferent innervation of the spinal cord (A) 3D reconstruction of an ear transplanted adjacent to the spinal cord labeled with antibodies against Tubulin (green) and MyoVI (red) displaying neurons and hair cells, respectively. (B-C) Single optical sections of an *X. laevis* brain and spinal cord (blue, autofluorescence) in the dorsal (B) and ventral (C) plane following injection of dye (green) into an adjacently transplanted ear shows afferents entering the spinal cord dorsally and ventrally, respectively. White arrowhead indicates the entry point of inner ear afferent projections. (D) Lateral view schematic diagram showing the position of the transplanted ear and the defined midline position (blue dotted line) along the dorsal-ventral axis of the spinal cord used to assign entry and projection planes of labeled afferents in B-C. (D') Analysis of entry point and plane of projection for animals with ears transplanted adjacent to the spinal cord. Serial optical sections were analyzed for entry point of labeled fibers (dorsal, midline, ventral) and for plane of projection (dorsal, ventral). n=20. (E) Backfilling of inner ear ganglion cells in an ear adjacent to the spinal cord from dye injection into the spinal cord rostral to the transplanted ear. (F) Backfilling (red) of inner ear ganglia and peripheral afferent processes on hair cells in an ear adjacent to the spinal cord from dye injection into the spinal cord. Hoechst nuclei counterstained in blue. Spinal Cord, SC; Hindbrain, HB; Dorsal, D; Ventral, V; Rostral, R; Ganglion cells, G; Utricle, U; Saccule, S; Lagena, L; Anterior canal, Ac; Horizontal canal, Hc; Posterior canal, Pc. Scale bars are 100 µm.

Since ear afferent connections with the spinal cord in identical transplants have been observed previously by retrograde labeling of ganglion cells from dye injection into the spinal cord, as well as in this study (FIG. 2A,E-F), afferent axon projections into the spinal cord were traced from the ear using lipophilic or dextran amine dyes. We aimed to determine if inner ear afferents from an ear transplanted adjacent to the spinal cord enter and project dorsally in the spinal cord as native afferent fibers do in the hindbrain.

Following labeling of afferent projections from the ear, the brain and spinal cord were dissected from the embryo and the entry point along the dorsal-ventral (D-V) axis of the spinal cord was determined (FIG. 2B-D). In assigning the D-V plane of entry, confocal scanning of the spinal cord along the entire D-V plane was used to define a midline position, where the middle of the z-series stack was considered neither dorsal nor ventral, while labeled afferents observed above or below this midline were considered to be dorsal and ventral entering, respectively (FIG. 2D). The majority of cases (14/20; 70%) had projections with a dorsal entry point, whereas five animals showed a ventral entry point and one animal had afferents enter at the midline (FIG. 2D').

Plane of fiber projection within the spinal cord was assessed in a similar manner and was defined by the D-V plane where fibers were observed to project once inside the spinal cord. Regardless of entry point, all 20 animals examined had afferents projecting dorsally within the spinal cord (FIG. 2D'). Additionally, these projections extended both rostral and caudal from the entry site. These results suggest that similar cues guide inner ear afferents in the hindbrain and spinal cord, consistent with known molecular conservation of dorso-ventral patterning in these areas of the CNS.

Ears Transplanted Adjacent to the Spinal Cord Project to the Hindbrain

Since ear afferent projections into the spinal cord appear to project dorsally regardless of entry point (FIG. 2), we next sought to identify if the afferent fibers projected into the hindbrain, and once within, if connections are established with the dorsally located vestibular nucleus, extending beyond past research showing such projections after ear transplantations adjacent to the hindbrain itself or adjacent to cranial nerves projecting to the hindbrain. In control animals, dye injection into the spinal cord (FIG. 3A) labels all ascending spinal tracts as well as trigeminal (V) nucleus afferents in the hindbrain (FIG. 3A'-B, green), as there exists a continuity between the hindbrain located descending tracts of V and ascending spinals. In animals with an ear transplanted next to the spinal cord, dye injection into the transplanted ear (FIG. 3C) also label dorsal ascending spinal tracts, as well as trigeminal tracts in the hindbrain (FIG. 3C'-D), suggesting that afferents from the transplanted ear fasciculate with ascending spinal tracts to enter the hindbrain and further continue along centrally-located trigeminal tracts (FIG. 3C'-D).

Figure 3:
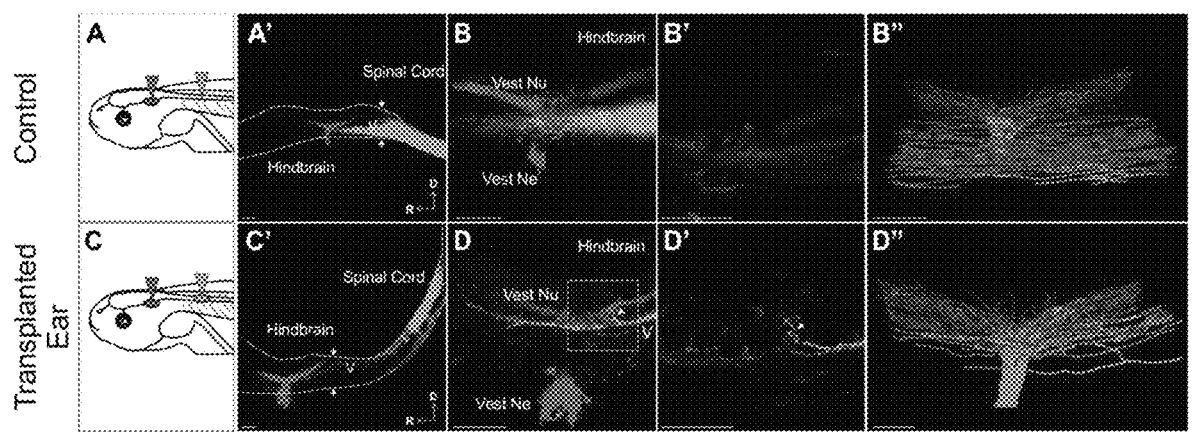
FIG. 3. Afferent innervation of the hindbrain by ears transplanted adjacent to the spinal cord (A) Schematic of dye placement for control animals. (A') Control hemisection of the brain and spinal cord showing ascending spinal fibers (green) enter the hindbrain and fill the descending tract of trigeminal nucleus (V, unlabeled). Native ear projections (red) into the vestibular nucleus in the hindbrain are labeled. Note the lack of overlap between the trigeminal nucleus and vestibular nucleus at higher magnification of A' (B) and of B, shown as a single optical section (B'). (B") 3D reconstruction of entire stack in B. (C) Schematic of dye placement for animals with ears transplanted adjacent to the spinal cord. (C') Hemisection showing ascending spinal tracts and spinal cord transplanted ear afferent fibers projecting into the hindbrain (green) along the descending tract of V (unlabeled). (D) Higher magnification of C' showing inner ear afferents projecting into the vestibular nucleus from the trigeminal nucleus (arrowhead). (D') Higher magnification of box in D showing projections into the vestibular nucleus (arrowhead) in a single optical section. (D") 3D reconstruction of entire stack in D. 8 experimental animals were analyzed. Arrows denote the hindbrain/spinal cord boundary. Scale bars are 100 μm in A',B,B",C',C",D and 50 μm in B', D'. Vest Ne vestibular nerve, Vest Nu vestibular nucleus, D dorsal, R rostral.

To determine whether these afferents from transplanted ears terminated in the dorsally located vestibular nucleus, dye was implanted into the native ears to label the vestibular nucleus (FIG. 3, red), providing a reference point with which to assess if transplanted inner ear afferents reroute from the more ventrally located trigeminal tracts they project with upon entering the hindbrain. In these transplanted ear animals, fibers apparently rerouted from the trigeminal tracts and into the vestibular nucleus upon reaching the hindbrain (FIG. 3C'-D"). Given the well-defined positions of sensory tracts and nuclei along the alar plate, closer examination showed that all 8 animals had fibers approaching and/or projecting directly into the vestibular nucleus. In contrast, in 8 control animals, no fibers from the spinal labeled tracts and hindbrain trigeminal tracts display any rerouting into the vestibular nucleus (FIG. 3A'-B"). Collectively these data show that inner ear afferents that enter the hindbrain from the spinal cord are capable of projecting to the vestibular nucleus, suggesting vestibular afferents are being navigationally instructed through yet unknown molecular cues once entering the hindbrain.

Transplanted Ears Make Functional Connections with the Hindbrain

Figure 4:
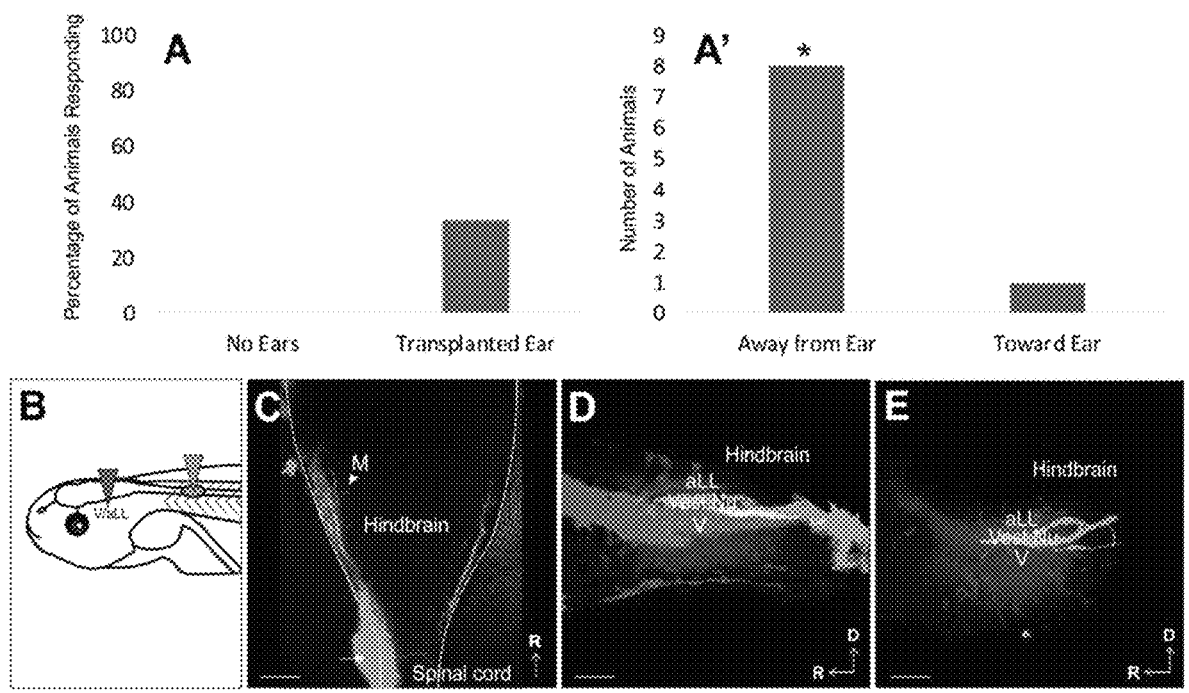
FIG. 4. C-Start Startle Response by Transplanted Ears. (A) Percentage of animals that displayed a C-start startle response following stimulation in control animals with no ears and in animals in which the only ear was the transplanted ear adjacent to the spinal cord. (A') Direction in each trial with a positive response observed in A from animals in which the only ear was the transplanted ear adjacent to the spinal cord. * $p<0.05$, Chi-Square analysis. (B) Schematic of dye placement. (C) Whole-mount of a hindbrain from an animal that had a response in all four trials, three were in the direction away from the transplanted ear and one in the direction toward the transplanted ear. Arrow designates entry point of transplanted inner ear afferents. M, Mauthner cell. (D) Lateral view of ipsilateral hemisected hindbrain showing projections of transplanted ear afferents (green) in between anterior lateral line (aLL) and trigeminal (V) afferent central projections (red). (E) Lateral view of contralateral hemisected hindbrain showing projections of a transplanted ear afferents (green) in between the region where the anterior lateral line (aLL) and trigeminal (V) nuclei are located. Autofluorescence is in blue. Scale bars are 100 μm.

To determine whether the inner ear afferents that reach the vestibular nucleus are making functional connections, behavioral and functional assays were conducted. To test for functional connections between the inner ear afferents of the transplanted ear and a second-order neuron in the vestibular nucleus of the hindbrain, the Mauthner cell, we utilized a C-start startle assay. We tested 13 control animals in which both native ears were removed, thus lacking any inner ear input, and 15 animals in which both native ears were removed but had an ear transplanted adjacent to the spinal cord. Attempts to elicit a C-start startle response in the thirteen control animals lacking all ears were unsuccessful (FIG. 4A). In contrast, in animals with an ear transplanted to the spinal cord and the native ears removed, eliciting a C-start startle response was successful in five of fifteen animals (FIG. 4A). Of these five animals, one animal responded in all four trials, one responded in two of four trials, and three animals responded in one of four trials. Of these nine trials that had responses, eight resulted in turns away from the transplanted ear and only one toward (FIG. 4A'). This was significantly different from an expected absence of directional bias ($p<0.05$). Given that wild type animals with both native ears turn in either direction with equal probability and those with one ear removed turn away from the remaining ear nearly every time, our data suggests that the ears transplanted adjacent to the spinal cord can develop functional connections within the vestibular nucleus that direct the movement of the tadpole away from the incoming stimulus from that ear. Furthermore, lipophilic dye tracing (FIG. 4B) of transplanted ears in these animals revealed inner ear afferents navigating to the vestibular nucleus in those animals that responded. In fact, the animal that responded in all four trials was the only one that had robust innervation of the ipsilateral vestibular nucleus and to a lesser degree, the contralateral vestibular nucleus (FIG. 4C-4E). This may explain why this animal had three turns away from the transplanted ear and one turn toward the transplanted ear. In addition, the Mauthner cell could be transcellularly labeled through the transplanted ear afferents (FIG. 4C), further supporting physical and functional contacts of these afferents with second order neurons in the vestibular nucleus.

Figure 5:
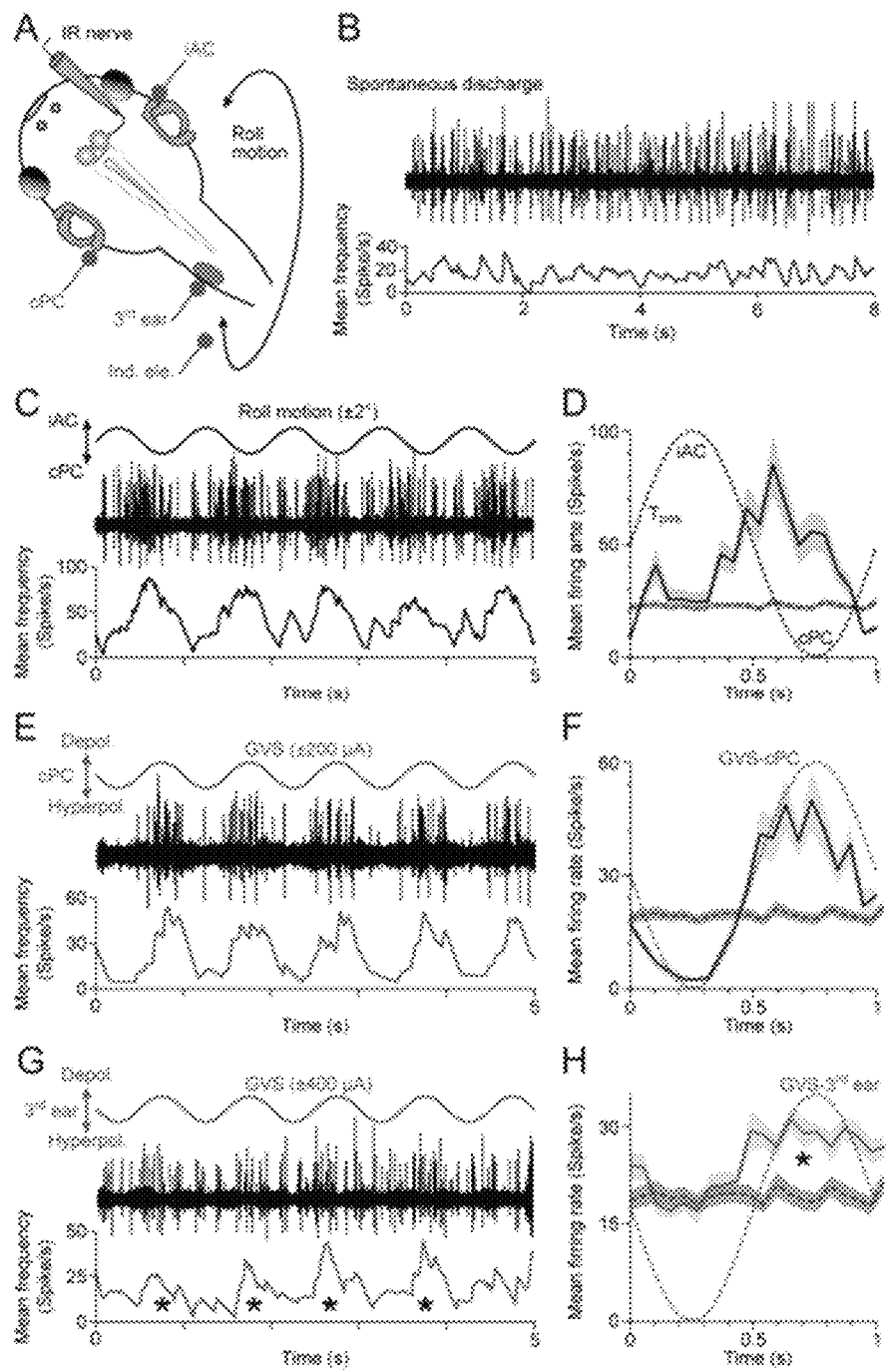
FIG. 5. Multi-unit inferior rectus (IR) nerve discharge during activation of native bilateral semicircular canals and a transplanted third ear on the spinal cord. (A) Schematic of a semi-intact *Xenopus* preparation depicting the recording of the right IR nerve during roll motion (black curved double arrow), galvanic vestibular stimulation (GVS) of the contralateral posterior (cPC) and ipsilateral anterior semicircular canal epithelia (iAC; red electrodes) and of the transplanted third ear (green electrodes). (B) Episode of spontaneous IR nerve discharge (black trace) with an average resting rate of ~20 spikes/s (blue trace) in an isolated preparation obtained from a stage 55 tadpole. (C,E,G) Modulated multi-unit discharge (black traces) and mean firing rate (lower colored traces) of the same IR nerve during roll motion in the cPC-iAC plane (C), during GVS of the cPC-iAC (E) and during GVS of the third ear (G); sinusoids indicate the waveform (1 Hz) for natural and galvanic stimulation. (D,F,H) Modulated mean IR nerve firing rate over a single cycle (black traces)±SEM (color-shaded areas) of the responses shown in C,E,G; the averages were obtained from 20-120 single cycles, respectively; the colored dotted sinusoids indicate the motion stimulus (D) and GVS of the cPC (F) and third ear (H), and the blue dashed line and horizontal band the mean±SEM resting rate of the IR nerve. Note that the IR nerve increases firing during motion in direction of the cPC (D), galvanic depolarization of the cPC epithelium (F) and galvanic depolarization of the third ear (* in G,H). Tpos, position signal of the turntable.

To further test for functional connections from the transplanted ear, a potential effective synaptic connection of the ascending fibers from the ectopic ear with the ipsilateral hindbrain vestibular network was tested in isolated, semi-intact preparations (Straka and Simmers, 2012), generated from animals with a transplanted ear at developmental stages 53-57. These in vitro preparations allow probing the performance of the vestibulo-ocular reflex (VOR) during natural motion stimulation or galvanic vestibular stimulation (GVS) of bilateral semicircular canal pairs. Accordingly, after disconnection from the target eye muscle, we recorded the multi-unit spike discharge of different extraocular motor nerves (n=15), such as the inferior rectus (IR) nerve (FIG. 5A,B) on both sides of the head in 5 transplanted animals. The average multi-unit resting discharge was similar between different extraocular motor nerves, ranged between 10-40 spikes/s (mean±SE; 28.7±3.8 spikes/s).

The multi-unit discharge of all recorded extraocular motor nerves exhibited a cyclic modulation during rotation (1 Hz and ±2° position oscillation; FIG. 5A) in a particular, eye muscle-specific spatial direction as indicated by the typical IR nerve discharge during roll motion (FIG. 5C,D). The multi-unit firing rate of the IR nerve was cyclically modulated during sinusoidal turntable motion along a plane formed by the ipsilateral anterior (iAC) and contralateral posterior semicircular canal (cPC). The discharge modulation of the IR nerve (FIG. 5C) essentially derived from a robust excitatory component, activated during motion in the direction of the cPC (FIG. 5D) and ranged for different extraocular motor nerves from 60-90 spikes/s. This motion-derived discharge modulation could be mimicked by sinusoidal GVS of the same bilateral semicircular canal pair, i.e. the iAC and cPC (FIG. 5E,F) at a frequency of 1 Hz and current amplitude of ±200 µA. The cyclic peak discharge occurred during galvanic depolarization of the cPC (FIG. 5F) and complied with the prediction from the phase relationship of the discharge modulation during motion stimulation (FIG. 5D). The peak discharge during GVS was usually smaller (40-70 spikes/s) compared to the motion-induced peak discharge but both response patterns comply in general with the typical functional organization of VOR circuits that consist of a crossed vestibular excitation and an uncrossed vestibular inhibition of extraocular motoneurons (Straka et al., 2014).

To evaluate if the transplanted ear is functionally connected to the native VOR circuitry, we applied sinusoidal GVS to the transplanted ear, clearly visible in all animals at the dorso-lateral aspect of the caudal tail region (see FIG. 5A). This allowed testing a possible activation of an extraocular motor response following stimulation of the ectopic ear. Indeed, in 10 out of 15 extraocular motor nerves recorded in 5 isolated preparations, sinusoidal GVS of the ectopic ear provoked a modulation of the spontaneous multi-unit discharge as exemplified in the contralateral IR nerve shown in FIG. 5G,H. The discharge modulation was robust across most trials (FIG. 5G) and ranged from 15-40 spikes/s in different extraocular motor nerves (mean±SE; 23.3±4.2 spikes/s; n=10). At variance with sinusoidal GVS of the native bilateral semicircular canal pair, the modulation consisted exclusively of an excitatory component as indicated by the lack of a disfacilitation below the resting discharge (see blue line in FIG. 5H).

The stimulus current intensity, necessary to evoke a modulated discharge was higher for the ectopic ear (±300 µA) compared to the native ears (±100 µA). Importantly, the discharge peak coincided with the depolarizing half cycle of the sinusoidal GVS (see green dotted line in FIG. 5H) and was confirmed by alternating trials with inversed current polarities. This current phase dependency of the evoked response is compatible with the functional requirements for activating neuronal tissue with this method and clearly indicates that the recruited hair cells and afferent fibers of the ectopic ear are connected to VOR projection neurons. Moreover, the increase in discharge suggests that the ectopic ear is predominantly connected to excitatory VOR neurons. This is compatible with the observation that an increased peak discharge during GVS of the ectopic ear occurred only in those extraocular motor nerves where the motoneuron somata was located contralateral to the transplanted ear, such as the IR nerve shown in FIG. 5. In contrast, in extraocular motor nerves with the motoneuron somata located ipsilateral to the ectopic ear (5 out of 15 extraocular motor nerves in 5 preparations), sinusoidal GVS failed to induce a noticeable discharge modulation. This differential pattern complies with the push-pull organization of the VOR assuming that the ectopic ear is only connected to excitatory VOR pathways or that potential connections with inhibitory pathways have a smaller modulatory efficacy.

Together, these results suggest, that while not successful all the time, some afferent projections from the transplanted ear into the vestibular nucleus are functional. Further work is needed to define the appropriate conditions which enable the formation of optimal functional connections (or their absence).

Fasciculation with Peripheral Nerves

Figure 6:
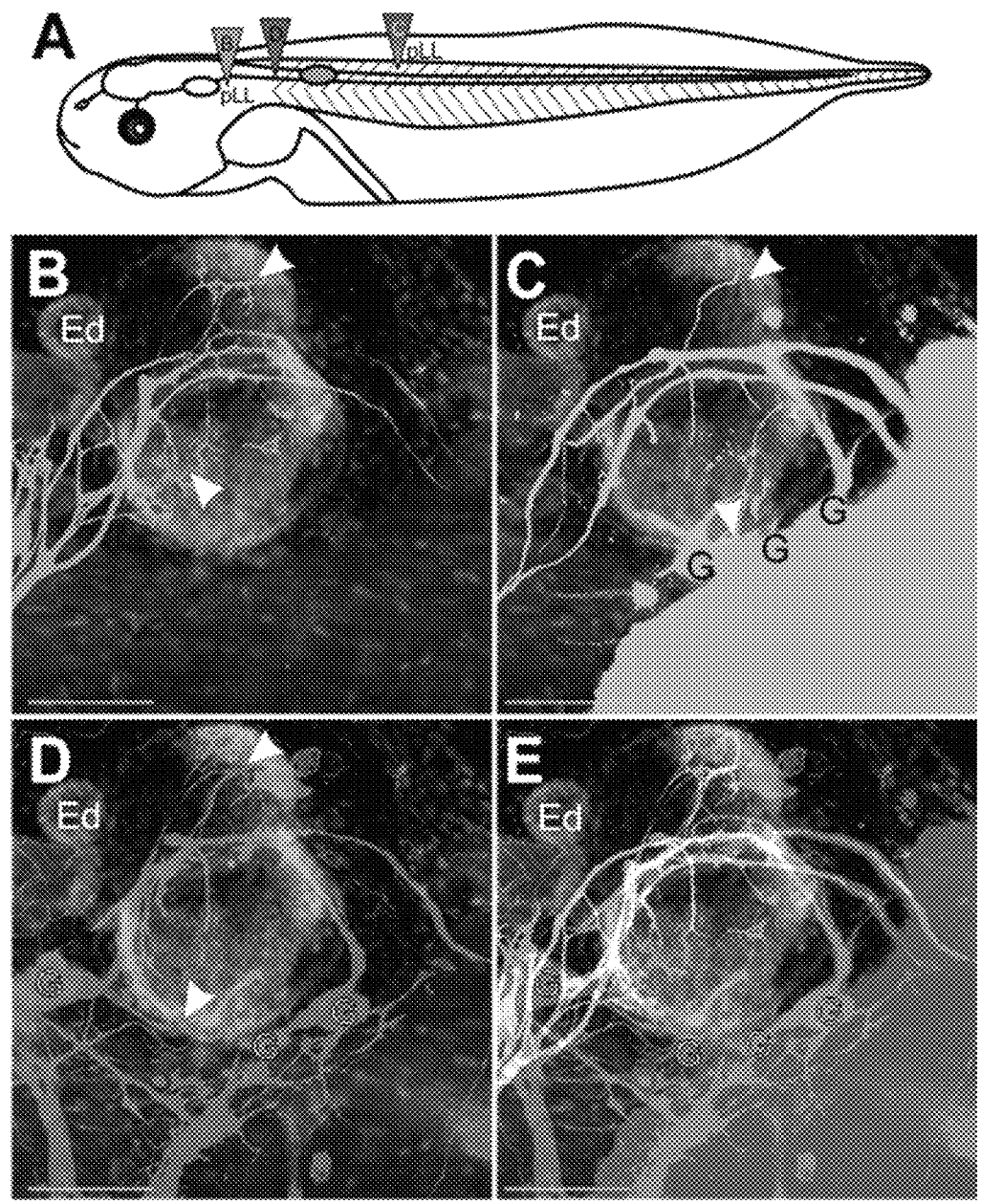
FIG. 6. Inner Ear Afferent Fasciculation with Lateral Line. (A) Schematic of dye placement for the different transplants. (B) Lateral view of ear transplanted adjacent to the spinal cord at stage 32-36 afferents of the pLL projecting over and into the ear (green, dye injection B in panel A). No ganglia were labeled. (C) Lateral view of pLL and inner ear afferents from a caudal dye injection into caudal portion of the pLL nerve (cyan, dye injection C in panel A). G, ganglia. (D) Lateral view of inner ear afferents from a spinal cord injection rostral to the transplanted ear (red, dye injection D in panel A) G, ganglia. (E) Merge of B-D. Cyan of panel C has been replaced by blue. Panels B-E are counterstained for nuclei marker Hoechst (gray). Arrowheads indicate areas of innervation of the inner ear. Scale bars are 100 μm.

Following a placodal origin in close proximity to native ears, pLL primordium migrate caudally toward the trunk and are found along the dorsal fin at stage 40. Given the caudal placement of the transplanted ear adjacent to the spinal cord, we next sought to identify if there would be an interaction with neurosensory components of the posterior lateral line (pLL) system. Specifically, are inner ear afferents able to navigate along the lateral line nerve and could lateral line afferents innervate the transplanted ear? Dye was placed into the pLL ganglia itself and into the pLL nerve caudal to the transplanted ear (FIG. 6A). Afferents of the pLL were observed to innervate the skin above the transplanted ear as well as continue a caudal trajectory past the ear along the dorsal fin (FIG. 6B), unlike in native ears where the skin above the ear is devoid of lateral line. Furthermore, pLL afferents were found to innervate the transplanted ear (FIG. 6B, arrowheads), as no inner ear ganglia were detected with the lipophilic dye from this injection. Placement of dye caudal to the transplanted ear, in the pathway of a more caudal segment of the pLL nerve, labeled inner ear ganglion cells (FIG. 6C), suggesting fasciculation between inner ear and pLL afferents. Furthermore, this caudal injection revealed innervation of the transplanted ear (FIG. 6C, arrowheads), most likely by inner ear afferents given the labeling of ganglia, though it cannot be ruled out additional contribution of lateral line to the innervation as well. Injection of dye directly into the spinal cord (FIG. 6A) labeled many more afferents and associated ganglia (FIG. 6D) than was labeled with a caudal application to the pLL nerve (FIG. 6C), though some afferents were labeled with both spinal cord and caudal lateral line dye applications (FIG. 6E). These data suggest that afferents of the inner ear are capable of projecting with peripheral nerves but do so as undirected growth along existing peripheral nerves.

Figure 7:
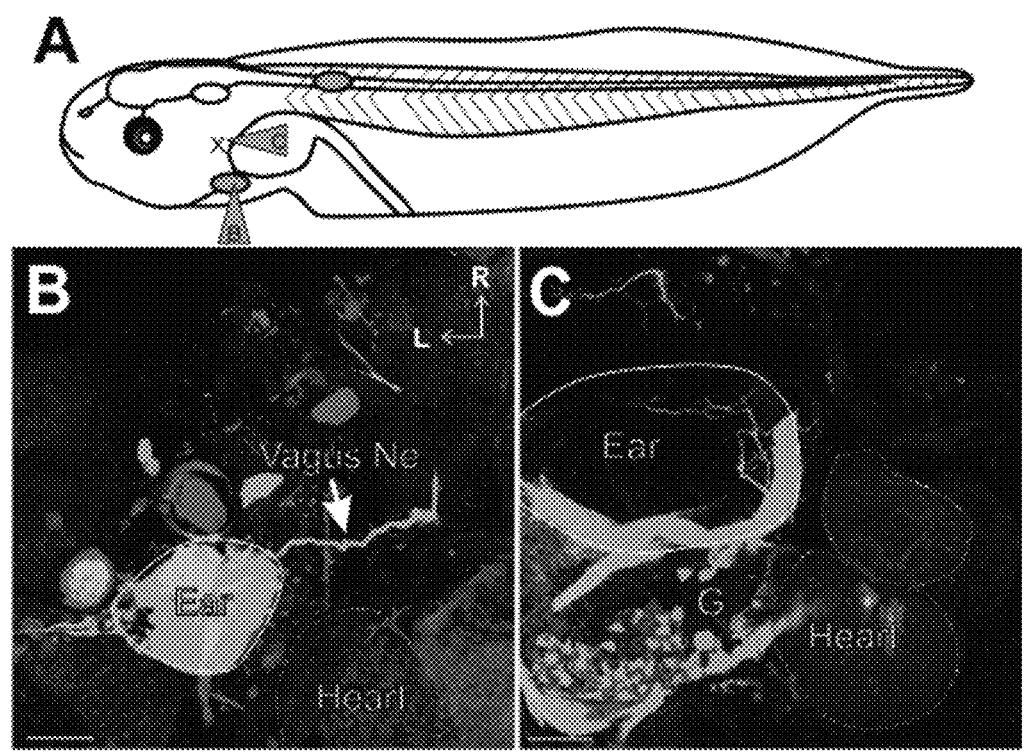
FIG. 7. Inner Ear Afferent Fasciculation with the Vagus nerve. (A) Schematic of dye placement for the different transplants. (B) Ventral view of an animal with an ear transplanted into the heart region showing ear afferents projecting with the vagus nerve (green, dye injection B in panel A; Vagus Ne, arrow). Heart is outlined with a dotted line as determined from autofluorescence background (blue). (C) Ventral view of an animal with an ear transplanted next to the heart. Labeling (green) from dye injection into the vagus nerve (dye injection C in panel A) showing innervation of the ear and labeling of inner ear ganglia. Autofluorescense background (blue). Scale bars are 100 μm.

To further test the possibility of fasciculation with any peripheral nerve bundles, we transplanted the ear ventrally into the region of the developing heart (FIG. 1C-D, FIG. 7B-C). Dye injections into the transplanted ear (FIG. 7A) identified afferents of the inner ear projecting with the vagus nerve (FIG. 7B). Furthermore, placement of dye into the vagus nerve (FIG. 7A) labeled ganglion cells of the transplanted ear, as well as their associated peripheral processes into the ear (FIG. 7C). These results further suggest that afferents of the inner ear are capable of fasciculation with any nearby peripheral nerve and that this potentially may be occurring without instructive signaling from nearby CNS sources.

Example 2

Methods

Animals

All animal work was conducted according to the Care and Use of Laboratory Animals and procedures were approved by the University of Iowa Institutional Animal Care and Use Committee (IACUC) (ACURF #1103057).

Fertilized chicken eggs were obtained from Hoover's Hatchery (Rudd, Iowa) and Aleta's Eggs (Belle Plaine, Iowa) and kept at 18° C. until incubation (maximum of 1 week at 18° C.). Eggs were incubated at 37° C. at 70% humidity for approximately 4 days prior to transplantation. Under our conditions, chicken embryos were between Hamburger-Hamilton (HH) stages 14-18 at the time of transplant, though most transplantations were performed between stages 16-18.

Wild type mouse embryos were obtained from pregnant females at embryonic day (E) 10.5. Pregnant females were anesthetized by injection of a lethal dose of Avertin (1.25% of 2.2.2-tribromoethanol at a dose of 0.025 ml/g of body weight) and decapitated. Uterine horns containing the mouse embryos were removed from the females and processed as described below.

Eggless Culture and Ear Transplantation

For our eggless culturing technique, we followed the general protocol of Cloney and Franz-Odendaal. Eggs were wiped with 70% ethanol and kept on their sides prior to cracking. Eggshells were cracked ventrally by tapping them against the narrow blunt end of a histological knife held securely in a microtome holder. Cut eggs were gently opened at the ventral cut and the content was decanted into a sterile weigh boat (88×88×23 mm; Fisher Scientific, catalog #08732113). Chickens were inspected for integrity of the yolk and only those with intact yolk were used as ear recipients. Those with ruptured yolks became ear donors.

For donors: For donor chickens, embryos (HH stage 14-18) were carefully cut free of the yolk with sterile dissection scissors and placed in sterile tissue culture medium (DMEM with LGlutamine, Fisher Scientific). For donor mice, embryos (E10.5) were carefully removed from the uterine horns and placed in sterile tissue culture medium (DMEM with LGlutamine, Fisher Scientific). For chicken and mice, the left and right otic vesicles were dissected out with sterile tungsten needles and placed in sterile tissue culture medium in a dish on ice for later transfer into a host. Dextran amine dye (Texas Red 3000MW, Molecular Probes) or methylene blue (Sigma) was added to the tissue culture medium to temporarily label the ears for ease of identification during transplantation. Time delay between ear removal from donor and implantation into host varied between 5-90 minutes with no apparent effect on donor ear development.

For hosts: The amnion around the HH stage 14-18 chicken embryo's head or torso was carefully opened with sterile forceps. A single otic vesicle (from chicken or mouse) was removed from the dish on ice and transferred to the host. For transplants adjacent to the hindbrain, the skin rostral to the native right ear was opened using sterile tungsten needles and the donor otic vesicle was pushed inside. For transplants adjacent to the spinal cord, the skin next to the spinal cord at the level of the forelimb bud was opened and the donor otic vesicle was pushed inside. Care was taken to orient the otocyst so that the endolymphatic duct pointed dorsal to avoid formation of enantiomorphic twins through rotation of ear axis relative to body axis.

A sterile Plexiglas lid was affixed to the weigh boat with scotch tape, 40 µl Penicillin/Streptomycin (5,000 units penicillin, 5 mg streptomycin per ml; Sigma, catalog # P4458) was added to the albumin, and the embryo culture was placed in the 37° C. incubator for an additional 1 to 5 days. The time of transplant as well as the stage of the host and the stage of the donor were recorded. Following the additional 1 to 5 days of incubation, embryos were fixed with 4% paraformaldehyde (PFA) through either immersion-fixation (1-2 day incubation) or through cardiac perfusion using a peristaltic pump followed by immersion (3-5 day incubation). Embryos were fixed at least overnight in 4% PFA before further processing.

Lipophilic Dye Labeling

Prior to injecting lipophilic dye, for some animals, heads were removed and hemisected to reveal the hindbrain. Small pieces of lipophilic dye-soaked filter paper (NeuroVue™ (Polysciences, Inc.) were flattened and implanted into the region of the vestibular nucleus in the alar plate between the native and transplanted ears (NeuroVue™ Maroon) to label afferents of the native and transplanted ears (FIG. 8G). In other animals, heads were removed from the fixed embryos and tissue carefully dissected away to reveal the inner ears. Lipophilic dye was implanted dorsally into the native (NeuroVue™ Red) and transplanted ears (NeuroVue™ Maroon) as well as into the trigeminal nerve (NeuroVue™ Jade) (FIG. 8F, 8H), either into the whole dorsal portion of the ear or into select vestibular sensory epithelia in the dorsal portion of the ear. On the contralateral/control (left) side of the animal, lipophilic dyes were implanted dorsally into the native ear (NeuroVue™ Red) and into the trigeminal (NeuroVue™ Jade) (FIG. 8F), either into the whole dorsal portion of the ear or into select vestibular sensory epithelia in the dorsal portion of the ear. Thus, with these placements of lipophilic dye, we should primarily label vestibular, rather than auditory, neurons. For ears transplanted to the spinal cord, skin was removed around the transplanted ear and lipophilic dyes were implanted into the transplanted ear (NeuroVue™ Maroon) and adjacent dorsal root ganglia (NeuroVue™ Red) (FIG. 8I).

Animals were placed in vials in 0.4% PFA and incubated at 60° C. for 2-5 days. For the chicken and mouse specimens labeled from the alar plate, Hoechst nuclear stain was added to the vials for the duration of the incubation. Dye diffusion was monitored daily with a fluorescent microscope to ensure proper diffusion over the distance. Ears or brains were mounted on a slide in glycerol. Brains were either whole-mounted or hemisected. Images were taken with a Leica TCS SP5 confocal microscope using Leica LB software.

Three-Dimensional Reconstruction

Transplanted ears from chicken and mouse were stained with Hoechst nuclear stain overnight. Ears were mounted in glycerol on a microscope slide. Confocal z-series images at 3 µm were taken of the ears using a Leica TCS SP5 confocal microscope. Z-series stacks were loaded into Amira Version 5.4 software for manual segmentation.

Results

Success of Transplantation

We transplanted 164 chicken ears and 54 E10.5 mouse ears into 218 chicken hosts, adjacent to the native ear. Of these, 59 hosts that received chicken ears and 11 that received mouse ears survived for several days until fixation (about 30%). Most of the chicken hosts that did not survive were lost within the first 12 hours (about 66% of all deaths), likely due to complications from bleeding or healing during the transplant process. The remainder died leading up to collecting, either due to infection or improper closing of the amnion. Following our establishment that 3-5 days post-transplant was the optimal time for afferent projection of both ears into the hindbrain (see below), we later only collected these stages, leading to a slight increase in animal loss as we were not fixing animals before amnion closure or before infection occurred. Since most causes of death were due to excess bleeding and to a lesser extent to infection of the albumin or improper closing of the amnion around the chickens, rather than a defect in the chickens themselves, we do not expect a survivorship bias in our assessments.

Figure 8:
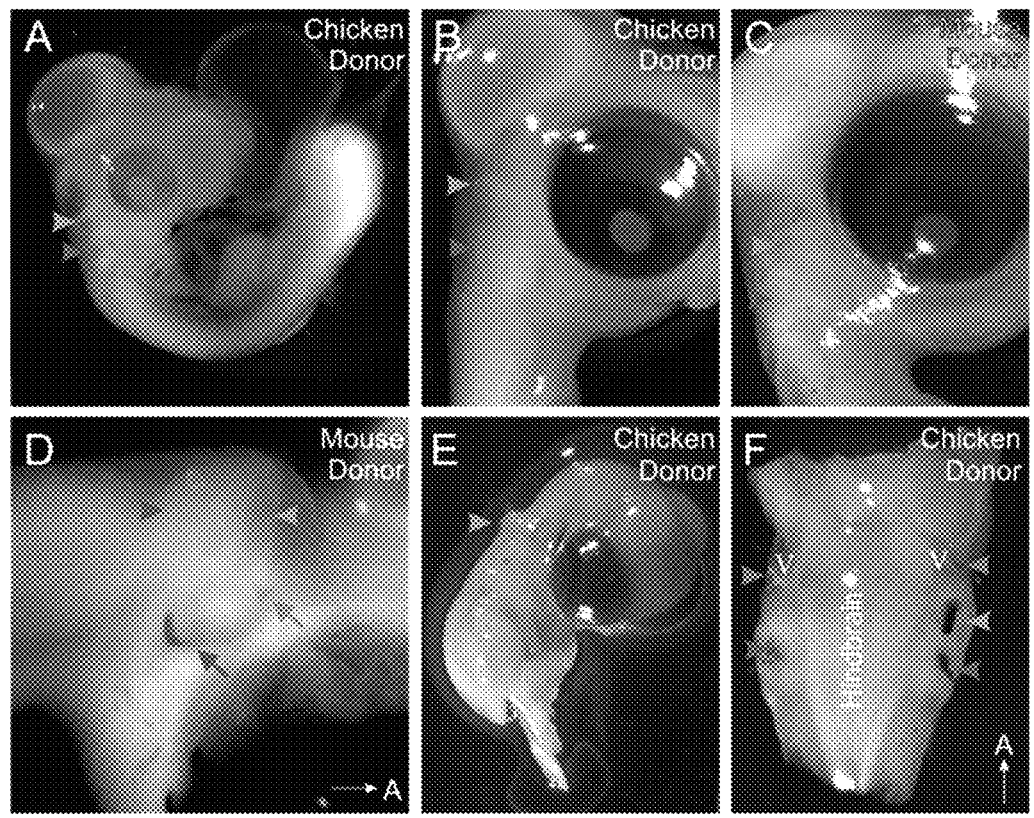
FIG. 8. Transplantations and dye labeling. (A) Chicken embryo with a donor chicken ear (green arrowhead) rostral to the native ear (red arrowhead) following two days of incubation. (B) Chicken embryo with a donor chicken ear (green arrowhead) rostral to the native ear (red arrowhead) following four days of incubation. (C) Chicken embryo with a donor mouse ear (green arrowhead) rostral to the native ear (red arrowhead) following five days of incubation. (D) Side view of dissected chicken head revealing a second external opening (green arrow) adjacent to the transplanted mouse ear (green arrowhead). The native ear and external opening are marked in red. (E) Chicken embryo with a donor chicken ear (green arrowhead) transplanted caudally to the trunk adjacent to the spinal cord. (F) Dorsal view of dissected chicken head showing placement of lipophilic dye into the transplanted ear (green arrowhead), native ears (red arrowheads), and into the trigeminal ganglia (V, magenta arrowheads). (G) Diagram depicting placement of lipophilic dye into the dorsal alar plate (green wedge) and subsequent neurons that would be labeled (Note: in some instances, the trigeminal ganglion was also labeled given the close proximity of the trigeminal nucleus to the vestibular nucleus (See FIG. 9C)). (H) Diagram depicting placement of lipophilic dye into the native ears (red wedge), transplanted ear (green wedge) and trigeminal ganglia (magenta wedge) and subsequent neurons that would be labeled. (I) Diagram depicting the placement of lipophilic dye into the transplanted ear (green wedge) and into dorsal root ganglia (DRG, red wedge) and the subsequent neurons that would be labeled.
Figure 8:
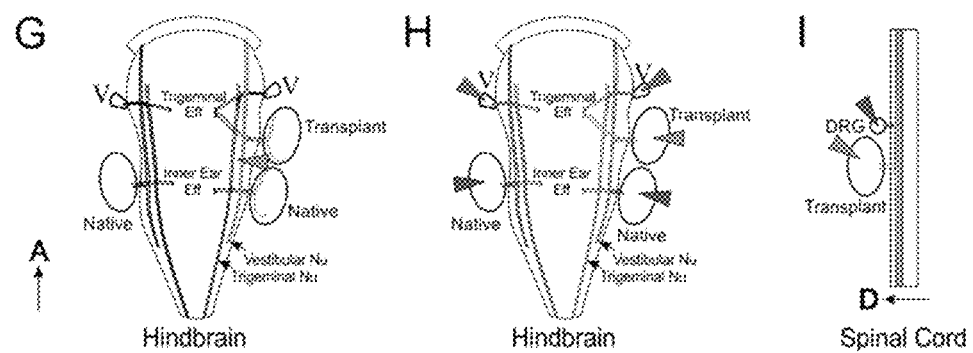

Successful transplantations were determined by the observed presence of an additional ear rostral to the native ear (FIG. 8). Of the 59 embryos receiving a chicken ear that survived until the designated fixation time, 54 had successful transplantations (FIG. 8A-B) and of the 11 embryos receiving a mouse ear that survived until fixation, all 11 had successful transplantations (FIG. 8C-D). In addition, we transplanted 38 chicken ears adjacent to the spinal cord. Of these, 13 survived until fixation and all 13 had successful transplantations (FIG. 8E). The best transplanted ears, where individual structures such as semicircular canals and cochlear/lagenar duct could be identified 21 at the later stages of fixation or those that were comparable in development to the native ears, based on the timing of transplant, at earlier stages of fixation were selected for further analysis.

Interestingly, at the time of fixation, we observed a second external ear opening immediately adjacent to the rostrally transplanted ears of both chicken and of mouse (FIG. 8D, arrows), indicating that the inner ear may serve as an organizer for middle and external ear components of the ear. For this study, we did not follow up on this possibility as we focused on the central projection and the differentiation of inner ear.

Transplanted Ears Develop Beyond Otocyst Stage

Figure 9:
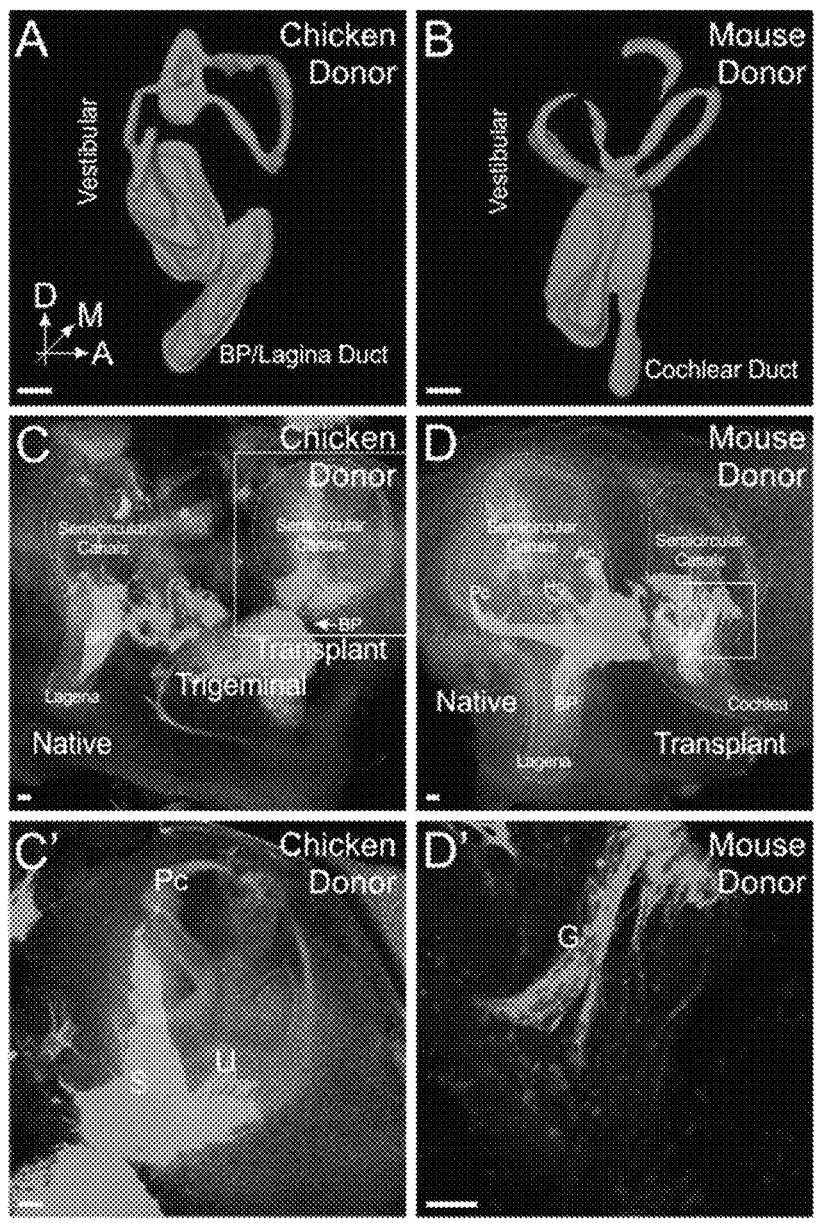
FIG. 9. Transplanted ears develop beyond otocyst stage. (A) Three-dimensional (3D) reconstruction of Hoechst staining of a chicken ear three days after transplant. (B) 3D reconstruction of Hoechst staining of a mouse ear four days after transplant. (C) Lipophilic dye labeling (green) from the alar plate and Hoechst (white) staining of a transplanted chicken ear four days after transplant showing innervation of the ears. The basilar papilla (BP, arrow)/lagena grew perpendicular to the plane of the image and is therefore not visible in this image or in E. (D) Lipophilic dye labeling (green) from the alar plate and Hoechst (white) staining of a transplanted mouse ear four days after transplant showing innervation of the ears. Semicircular canals (Ac, anterior, Pc, posterior, Hc, horizontal) are labeled in the native chicken ear. (C') Higher magnification of C (boxed area) showing innervation of the posterior canal (Pc) utricle (U) and saccule (S) from the transplanted ear. (D') Higher magnification of D (boxed area) showing otic ganglia (G) adjacent to the mouse ear. Orientation for all panels is as in A (A, anterior, D, dorsal, M, medial). Scale bars represent 100 µm.

To determine the degree of development of the transplanted ears, ears were stained with Hoechst nuclear stain (n=7 each for chicken and mouse) and subsequently 3D reconstructed 28. While there was some variation in overall morphology, in general, transplanted ears of both chicken and mouse were found to have developed beyond the otocyst stage. Both transplanted chicken and mouse ears develop dorsal vestibular and ventral auditory components (FIG. 9A-B). In each specimen examined with Hoechst staining, we were able to observe semicircular canals as well as the lagenar/cochlear duct (FIG. 9A-B).

In addition, injection of lipophilic dye into the vestibular nucleus region of the alar plate of the hindbrain (FIG. 8G) provided visualization of the afferent innervation of the ears (n=2 each for chicken and mouse; FIG. 9C-D'). Furthermore, this method demonstrated otic ganglia formed adjacent to the developing ears (FIG. 9D') that connected ears to the alar plate of the hindbrain consistent with known afferent and efferent connections in vertebrates. Together these results show that in our ex-ovo culturing system, chicken and mouse ears do develop following transplantation, including inner ear ganglion neurons that project with their afferents to the hindbrain alar plate. However, while present at the later times of analysis, the auditory system in both transplanted chicken and mouse ears is not as completely developed as the vestibular, especially at some of the earlier stages we collected. Thus, for the remainder of our experiments, the dorsal vestibular portions of the ears were labeled with lipophilic dye and thus we are primarily looking only at vestibular projections for the remainder of the study.

Inner Ear Afferents from Transplanted Chicken Ears Project to the Vestibular Nuclei Regardless of Timing or Entry Point We first determined the time at which afferents from the transplanted ear could be labeled in the hindbrain (Table 1). In age-matched transplants, we labeled afferents from about half of transplanted ears following one or two days of incubation after transplant (n=1/2 and 5/8, respectively), and always labeled afferents three days after transplantation. Furthermore, the animal in which afferents from the transplanted ear could be labeled in the hindbrain following one day of incubation had very little hindbrain projection compared with the native ears. In contrast, afferents from the native ears were consistently labeled both one and two days after transplant (n=2/2 and 8/8, respectively). This suggests that there is a slight delay between timing of entry between the two ears, even when the donor ear was at the same stage as that of the host.

TABLE 1

| Timing of entry into the hindbrain | | |
| --- | --- | --- |
| Days Post Transplant | Transplanted Ear | Native Ear |
| 1 | 1/2 | 2/2 |
| 2 | 5/8 | 8/8 |
| 3 | 2/2 | 2/2 |
| 4 | 2/2 | 2/2 |

Numbers represent animals in which dye-labeled inner ear afferents could be detected in the hindbrain.

Figure 10:
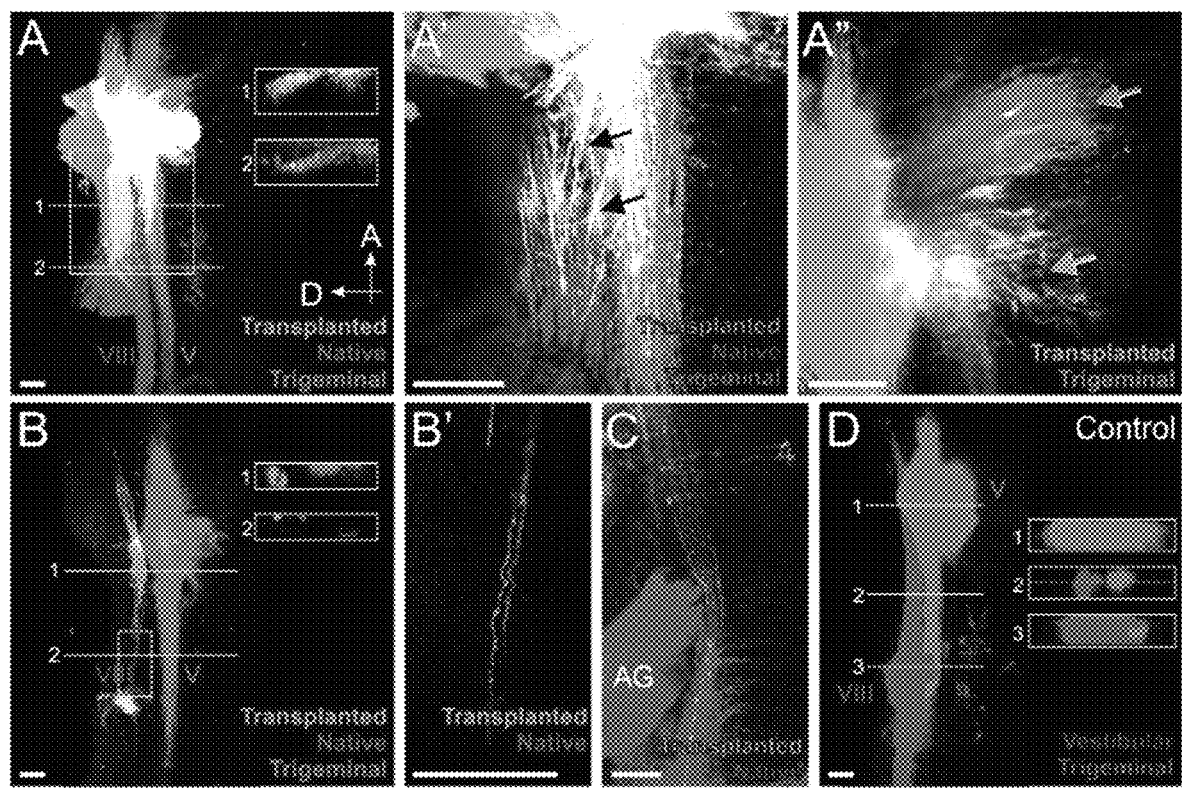
FIG. 10. Afferents from transplanted chicken ears project to the vestibular nucleus regardless of timing or entry point. (A) Central projections of a transplanted chicken ear (green), native chicken ear (red), and trigeminal (magenta). Afferents from the transplanted ear enter with the trigeminal nerve (observed in 3/10 animals). Insets are single orthogonal sections through the z-dimension at the locations of the dotted lines in A. (A') Single optical section of boxed area in A showing that inner ear afferents from the transplanted ear reroute from the trigeminal nucleus to the vestibular nucleus (arrows). (A") Single optical section of the trigeminal motor nucleus in A showing, through backfilling of lipophilic dye, a subpopulation of trigeminal motor neurons projecting to the transplanted ear (green arrow). Magenta arrow designates motor neurons filled with trigeminal application of lipophilic dye. (B) Central projections of a transplanted chicken ear (green), native chicken ear (red), and trigeminal (magenta). Afferents from the transplanted ear enter separate from the trigeminal nerve (observed in 7/10 animals). Insets are single orthogonal sections through the z-dimension at the locations of the dotted lines in B. Arrowheads indicate position of single axons highlighted in B'. (B') Single optical section of boxed area in B showing projection of afferents from the transplanted ear together with afferents from the native ear. (C) Central projections of a transplanted chicken ear (green) and native chicken ear (red) from an animal with a heterochronic transplant. AG, auditory ganglia. (D) Single optical section of a control projections of a native inner ear (red) and trigeminal (magenta). Insets are single orthogonal section through the z-dimension at the location of the dotted lines in D. Dotted line in inset 2 shows the location of the optical section in D. V, trigeminal nucleus; VIII, vestibular nucleus; Orientation for all panels is as in A (A, anterior, D, dorsal). Scale bars represent 100 µm.

To determine whether the timing of entry affects pathfinding, we transplanted donor chicken ears rostral to the native host ear (FIG. 8B) and at different time points. Using different colored lipophilic dye-soaked filter paper implanted into both the native and transplanted ears, as well as the trigeminal ganglion (FIG. 8F, 8H), we found that afferents from the transplanted ears project to the vestibular nuclei from animals with age-matched donor ears at all stages examined that we could detect lipophilic-labeled afferents in the hindbrain (n=8/8; FIG. 10A-B). In addition, we found afferents projecting to the vestibular nuclei in animals with ears transplanted from younger donors (HH 15-16 to HH 17-18; n=2/2; FIG. 10C), suggesting that these slight delays in afferent entry into the hindbrain by a transplanted ear does not affect pathfinding, at least for the stages examined here. As a reference, we also implanted different colored lipophilic dyes into the native ear and trigeminal afferents on the side contralateral to the transplantation. Those tracings revealed direct projection of vestibular and trigeminal fibers to their respective nuclei in the hindbrain (n=10/10, FIG. 10D), showing that under normal circumstances, inner ear afferents project directly to the vestibular nuclei adjacent and dorsal to trigeminal afferents. These data confirm previous work showing that afferents from different sensory organs project always directly to their specific nuclei, suggesting afferent specific attractive cues within the hindbrain.

Upon closer examination of projections of transplanted ears, we observed that afferents from the transplanted ear either enter with their own entry point between the entry point of the native ear and that of the trigeminal nerve or enter together with the trigeminal afferents at the trigeminal entry point in Rhombomere 2. Afferents from the transplanted ear that entered with their own entry point (n=7/10) invariably projected directly to the vestibular nucleus, together with afferents labeled from the native ear (FIG. 10B-B'). To our knowledge, this is the first time that the ability of inner ear afferents to digest their way through the neural crest derived meninges covering the developing hindbrain has been reported. This ability is in line with such abilities of neural crest derived cranial nerve afferents, but contrasts to trigeminal branchial motor neurons that cannot leave the hindbrain in the absence of meningeal foramina generated by trigeminal afferents. In contrast, if the afferents from the transplanted ear navigated along trigeminal afferents and entered together with them (n=3/10), only some fibers immediately project dorsally to the vestibular nucleus together with afferents from the native ear and the remaining fibers project for a short distance with trigeminal afferents (FIG. 10A-A'). However, while the remaining fibers fasciculate initially with trigeminal afferents, they eventually segregated from the trigeminal afferents and rerouted into the vestibular nucleus between Rhombomeres 2 and 4 (n=3/3; arrows, FIG. 10A'). These data suggest that afferents are molecularly attracted over short distances to the vestibular nucleus territory and this attraction can overcome the fasciculation with trigeminal afferents. Time lapse images of growing fibers are needed reveal the details of choices made by navigating fibers to go beyond the suggestions derived from our stills that demonstrate the segregation from trigeminal fibers only after the fact.

Transplanted Chicken Ears Receive Trigeminal Branchial Motor Neuron Innervation

In addition to labeling inner ear afferents, implantation of lipophilic dye into the transplanted ear revealed retrogradely filled basal plate branchial motor neurons within the trigeminal motor nuclei (FIG. 10A″), suggesting that these motor neurons reroute to the transplanted inner ear. Trigeminal branchial motor neurons labelled from the transplanted ear were observed in all animals in which the trigeminal motor population was labeled (n=5/5). Furthermore, entry point of the transplanted ear afferents did not appear to affect the ability of trigeminal motor neurons to reroute to the transplanted ears. Labeled cell bodies in the trigeminal motor nucleus were found both in animals in which afferents from the transplanted ear entered the hindbrain with their own entry point (n=3/5) and also in animals in which the afferents from the transplanted ear entered together with the trigeminal nerve (n=2/5).

Figure 11:
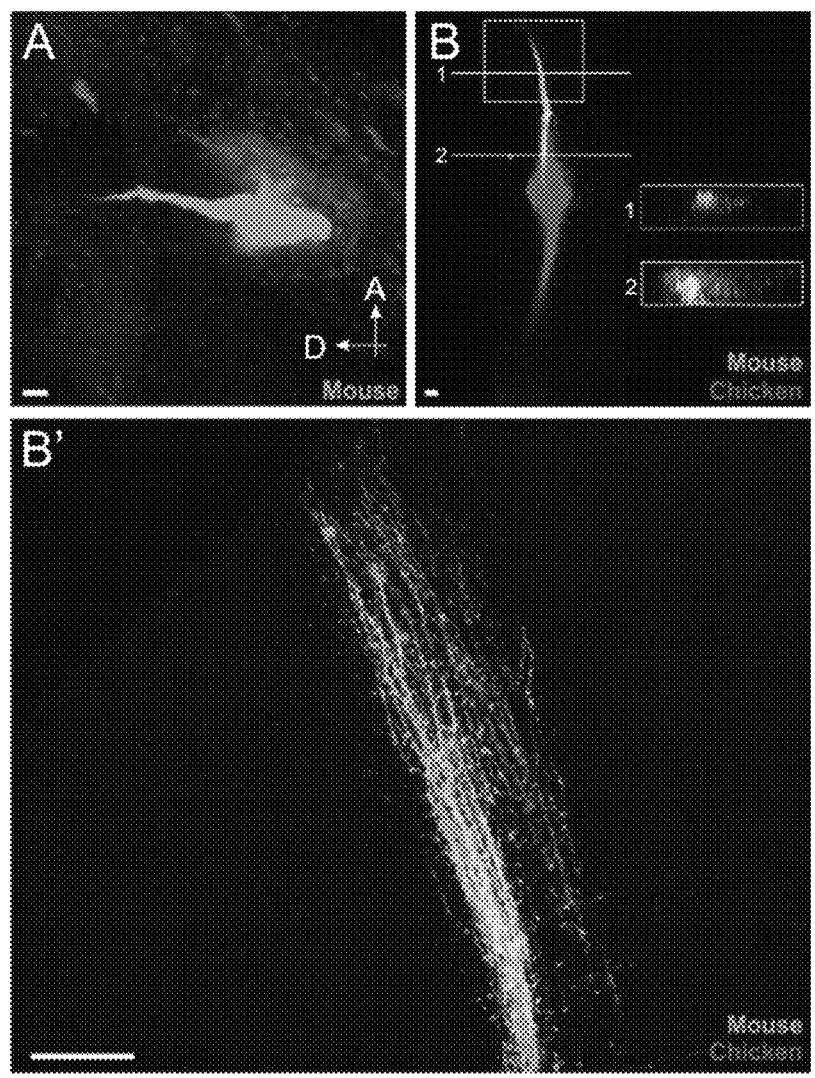
FIG. 11. Afferents from transplanted mouse ears project to the vestibular nucleus of a chicken. (A) Lipophilic dye labeling of a transplanted mouse ear showing directed projections of the afferents exiting the mouse ear (green) dorsally toward the hindbrain of the chicken. (B) Central projections of a transplanted mouse ear (green) and native chicken ear (red). Insets are single orthogonal sections through the z-dimension at the locations of the dotted lines in B. (B') Single optical section of boxed area in B showing projection of afferents from the transplanted mouse ear together and in the same plane as afferents from the native chicken ear (observed in 4/4 animals). Orientation for all panels is as in A (A, anterior, D, dorsal). Scale bars represent 100 µm.

Inner Ear Afferents from Transplanted Mouse Ears Project Directly to the Vestibular Nuclei To determine whether inner ear afferents navigate using a set of guidance molecules that is conserved across amniote species, we transplanted mouse embryo otocysts rostral to the native ear of chicken embryos (FIG. 8C-D). Implantation of lipophilic dyes into the mouse ear revealed that mouse afferents projected directly towards the hindbrain (FIG. 11A). That the mouse afferents did not project in a random or disordered manner indicates that these mouse inner ear afferents are targeted directly toward the hindbrain of the chicken, comparable to transplanted chicken ears. Alternatively, this could indicate that only the afferents that reached the brain remained at the late stage when we analyzed them.

Comparison of central projections of afferents from the transplanted mouse ear with that of the native chicken ear through lipophilic dye labeling of the both mouse and chicken ears revealed that mouse inner ear afferents projected to the chicken vestibular nucleus (n=4/4, FIGS. 11B-B'). Examination of single optical sections indicate that the mouse inner ear afferents project in the same dorsoventral column as native chicken inner ear afferents (FIG. 11B'). These data indicate that mouse inner ear afferents are molecularly guided to the corresponding chicken nuclei, suggesting conservation of molecular guidance between those two amniote species that each evolved for over 300 million years from their last common ancestor.

Figure 12:
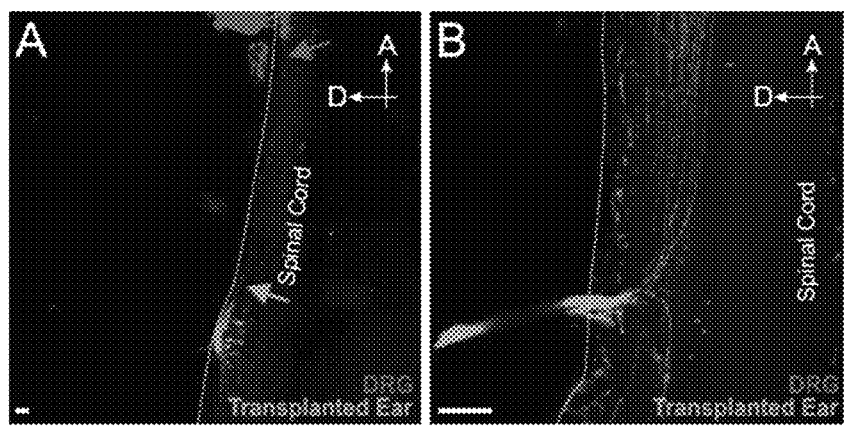
FIG. 12. Afferents from transplanted chicken ears project dorsally in the spinal cord. (A-B) Lipophlic dye labeling of the transplanted ear (green) and dorsal root ganglia (red) from two different animals show that transplanted ear afferents project dorsally in the spinal cord. Arrows in A indicate projections of the transplanted ear (green arrow) and dorsal root ganglia (red arrow). Scale bar represents 100 µm.

Inner Ear Afferents from Ears Transplanted to the Spinal Cord Project Dorsally Even in the Absence of any Vestibular or Auditory Nuclei Knowing that the pattern of gene expression and diffusible morphogen gradients in the hindbrain, which is conserved across species, is also conserved with the spinal cord we transplanted donor chicken otocysts to the trunk, adjacent to the spinal cord (FIG. 8D). Importantly, spinal cords develop neither vestibular nor cochlear nuclei thus allowing us to exclude additional attractions mediated from neurons of those nuclei. Implantation of lipophilic dye into the transplanted ear and into adjacent dorsal root ganglia (FIG. 8I) revealed that the transplanted ear projected in the most dorsal position of the spinal cord, at the same level or dorsal to the dorsal root ganglia projections (n=5/5, FIG. 12A-B). Since dorsal root projections are consistent with the descending tract of V (trigeminal), suggests inner ear afferents are targeted to a more dorsal position, as they are in the hindbrain. These data indicate that the inner ear afferents are possibly targeted by conserved molecular guidance cues across craniate chordates defining dorsal such as Wnts, BMPs and Lmx1a and not simply attracted to vestibular nuclei.

In summary, our transplantation demonstrated that transplanted ears of chicken and mice target primarily dorsal areas of hindbrain and spinal cord. The dorsal spinal cord projection in the absence of vestibular or auditory nuclei formation supports that inner ear afferents orient using diffusible molecules setting up dorsoventral gradients to pattern hindbrain and spinal cord and are not attracted by molecules released from vestibular nuclei, expanding our observation on auditory afferent targeting in the absence of cochlear nuclei.

Although the disclosure has been described with reference to preferred embodiments, persons skilled in the art will recognize that changes may be made in form and detail without departing from the spirit and scope of the disclosed apparatus, systems and methods.

What is claimed is:

1. A method for treating or restoring hearing and/or balance loss in a subject in need thereof, comprising: transplanting a otocyst to a target delivery site of the subject, wherein the otocyst is obtained from a species that is different from the subject species and wherein prior to transplantation, the otocyst is cultured in a tissue culture buffer.

2. The method of claim 1, wherein the otocyst is obtained from a non-human mammal embryo.

3. The method of claim 2, wherein the non-human mammal is a pig.

4. The method of claim 1, wherein the delivery site is the vestibule of the inner ear of the subject.

5. The method of claim 4, further comprising removing of the stapes footplate of the subject, prior to the transplantation of the otocyst.

6. The method of claim 5, further comprising implanting an osseointegrated bone conduction hearing aid.

7. The method of claim 1, wherein the delivery site is the internal auditory canal of the subject.

8. The method of claim 1, wherein the delivery site is the cerebellopontine angle adjacent to axons of cranial nerve VIII.

9. The method of claim 1, wherein the delivery site is proximate to the jugular foramen.

10. The method of claim 9, wherein the delivery site is adjacent to the rootlets of cranial nerves IX and X.

11. The method of claim 10, further comprising exposing the delivery site by performing a retrosigmoid or infratemporal fossa craniotomy on the subject.

12. The method of claim 1, wherein the dorsoventral, mediolateral, and anteroposterior orientation of the otocyst is maintained relative to the target delivery zone of the subject.

13. The method claim 1, further comprising implanting a cochlear implant electrode to activate the inner ear.

14. The method of claim 1, further comprising implanting an osseointegrated bone conduction hearing aid.

* * * * *